(12) United States Patent
Seok et al.

(10) Patent No.: US 10,261,541 B2
(45) Date of Patent: Apr. 16, 2019

(54) CURVED BODY AND WEARABLE DEVICE THEREWITH

(71) Applicant: Samsung Electronics Co., Ltd., Gyeonggi-do (KR)

(72) Inventors: Sang-Youp Seok, Gyeongsangbuk-do (KR); Byoung-Uk Yoon, Gyeonggi-do (KR); Min-Sung Lee, Gyeonggi-do (KR)

(73) Assignee: Samsung Electronics Co., Ltd., Yeongtong-gu, Suwon-si, Gyeonggi-do (KR)

( * ) Notice: Subject to any disclaimer, the term of this patent is extended or adjusted under 35 U.S.C. 154(b) by 0 days.

(21) Appl. No.: 15/875,210

(22) Filed: Jan. 19, 2018

(65) Prior Publication Data

US 2018/0143663 A1 May 24, 2018

Related U.S. Application Data

(63) Continuation of application No. 15/375,347, filed on Dec. 12, 2016, now Pat. No. 9,886,059, which is a
(Continued)

(30) Foreign Application Priority Data

Feb. 22, 2014 (KR) ........................ 10-2014-0020974

(51) Int. Cl.
*G06F 1/16* (2006.01)
*H05K 5/00* (2006.01)
(Continued)

(52) U.S. Cl.
CPC ............ *G06F 1/163* (2013.01); *A61B 5/0002* (2013.01); *A61B 5/0404* (2013.01);
(Continued)

(58) Field of Classification Search
CPC ...... G06F 1/1686; G06F 1/163; G06F 1/1635; G06F 1/1637; A61B 5/04; A61B 5/0404;
(Continued)

(56) References Cited

U.S. PATENT DOCUMENTS

| 4,819,860 A * | 4/1989 | Hargrove ........... A61B 5/02055 128/903 |
| 6,529,754 B2 * | 3/2003 | Kondo ............... A61B 5/02438 600/335 |

(Continued)

FOREIGN PATENT DOCUMENTS

| CN | 101473362 A | 7/2009 |
| CN | 101890217 A | 11/2010 |

(Continued)

OTHER PUBLICATIONS

"Hands on with the new Garmin Vivofit & Vivoki Activity Monitors"; Garmin Product Reviews; Jan. 6, 2014; DC Rainmaker, 26 pages; XP-002773018.
(Continued)

*Primary Examiner* — Anthony M Haughton
(74) *Attorney, Agent, or Firm* — Cha & Reiter, LLC.

(57) ABSTRACT

A wearable device may include: a strap including a substantially polygonal opening and a buckle formed at one end thereof; a buckle part configured to fasten opposite ends of the strap to each other by binding the opposite ends of the strap; and a body configured to be coupled to the opening by being fitted into the opening or decoupled from the opening. The body may include a front surface and a rear surface, and a display having a substantially polygonal shape when viewed from the top on the front surface, and a biometric sensor disposed on the rear surface.

22 Claims, 27 Drawing Sheets

Related U.S. Application Data continuation of application No. 15/367,615, filed on Dec. 2, 2016, now Pat. No. 9,874,901, which is a continuation of application No. 14/628,575, filed on Feb. 23, 2015, now Pat. No. 9,639,119.

(51) Int. Cl.

| | | |
|---|---|---|
| *H05K 7/00* | (2006.01) | |
| *A61B 5/0404* | (2006.01) | |
| *A61B 5/0476* | (2006.01) | |
| *A61B 5/0488* | (2006.01) | |
| *A61B 5/00* | (2006.01) | |
| *A61B 5/0402* | (2006.01) | |

(52) U.S. Cl.
CPC .......... *A61B 5/0476* (2013.01); *A61B 5/0488* (2013.01); *A61B 5/681* (2013.01); *G06F 1/1635* (2013.01); *G06F 1/1637* (2013.01); *A61B 5/0402* (2013.01); *A61B 2560/0443* (2013.01); *A61B 2562/0219* (2013.01)

(58) Field of Classification Search
CPC . A61B 5/04004; A61B 5/0476; A61B 5/0488; A61B 5/68; A61B 5/681; A61B 5/6801; A61B 5/6802
USPC .......................... 361/679.01, 679.02, 679.03
See application file for complete search history.

(56) References Cited

U.S. PATENT DOCUMENTS

| | | | | |
|---|---|---|---|---|
| 8,477,981 B2* | 7/2013 | Heck | ...................... | G04G 21/06 381/333 |
| 9,110,498 B2* | 8/2015 | Martinez | ................ | A61B 5/681 |
| 2002/0141775 A1* | 10/2002 | Mitsuoka | ........... | G03G 15/2042 399/69 |
| 2002/0151775 A1 | 10/2002 | Kondo | | |
| 2008/0002528 A1* | 1/2008 | Andren | ................ | G04G 17/045 368/241 |
| 2010/0292599 A1* | 11/2010 | Oleson | ............... | A63B 24/0062 600/519 |
| 2011/0007468 A1* | 1/2011 | Burton | .................... | G04F 10/00 361/679.03 |
| 2013/0329532 A1* | 12/2013 | Sorias | ..................... | G04C 10/00 368/64 |
| 2014/0121539 A1* | 5/2014 | Chatterjee | ............. | G06F 1/1626 600/479 |
| 2015/0049591 A1* | 2/2015 | Adams | ................... | G04G 21/08 368/13 |
| 2015/0189134 A1* | 7/2015 | Joo | ......................... | G06F 1/163 348/373 |
| 2015/0223355 A1* | 8/2015 | Fleck | ...................... | G06F 1/163 361/679.03 |
| 2015/0241916 A1* | 8/2015 | Choi | ....................... | G06F 1/163 361/679.03 |
| 2016/0066859 A1* | 3/2016 | Crawford | ............. | A61B 5/7264 600/301 |
| 2016/0078061 A1* | 3/2016 | Hilsdale | .............. | G06F 19/3418 707/687 |

FOREIGN PATENT DOCUMENTS

| | | |
|---|---|---|
| KR | 10-2007-0105107 A | 10/2007 |
| KR | 10-2010-0050406 A | 5/2010 |

OTHER PUBLICATIONS

"Misfit Shine"; chosun.com; Aug. 28, 2013.
Zhang Li; "Misfit Shine Review: Maybe the best bracelet at the moment"; http://tech.qq.com/a/20131031/008008.htm; Oct. 31, 2013.
"Hands on with the new Garmin Vivofit & Vivoki Activity Monitors"; Jan. 6, 2014; DC Rainmaker; pp. 1-21.
Chinese Search Report dated Jul. 23, 2018.

* cited by examiner ered Serial
CURVED BODY AND WEARABLE DEVICE THEREWITH

CROSS REFERENCE TO RELATED APPLICATIONS

This application is a Continuation of U.S. patent application Ser. No. 15/375,347 filed on Dec. 12, 2016 which claims the benefit of the earlier U.S. patent application Ser. No. 15/367,615 filed on Dec. 2, 2016 which in turn claims a priority to an U.S. patent application Ser. No. 14/628,575 filed on Feb. 23, 2015 and assigned U.S. Pat. No. 9,639,119 issued on May 2, 2017 which claims, pursuant to 35 U.S.C. § 119(a), priority to and the benefit of the earlier filing date of a Korean Patent Application filed in the Korean Intellectual Property Office on Feb. 22, 2014 and assigned Serial No. 10-2014-0020974, the entire contents of which are incorporated herein by reference.

BACKGROUND

1. Technical Field

The present disclosure generally relates to an electronic device that is worn on a human body.

2. Description of the Related Art

Methods for a user to carry a portable electronic device include carrying a the device in the user's pocket or bag, holding the device in the user's hand, or carrying the device by wearing it on a predetermined location of a human body. A wearable device can be worn on various parts of the human body and used.

Wearable devices may be worn on the human body in various ways as follows:

1. A wearable device may be worn on a human body such as a wrist like a watch or band;
2. A strap-type wearable device may be worn on a human body like a necklace; and
3. A glasses-type wearable device may be worn on user's face;
4. A clip-type wearable device may be worn by being clipped to a human body, clothing, or user's belongs; and
5. There are many other methods for attaching a wearable device to a human body, belongs, or an accessory directly or indirectly.

In addition, a wearable device may include a body and a wearing part (a strap or band), and may be worn on various parts of a human body according to a configuration of the wearing part. The wearable device may be one of the following structures:

1. a structure in which the body and the wearing part are integrally formed with each other and inseparable from each other;
2. a structure in which the body and the wearing part are separable from each other and thus are changeable.

Currently available wearable devices have several deficiencies. For example, the body of the wearable device is mostly designed regardless of design aspects and the exterior of the body and the inner wearing part are mostly formed according to the same flat/curved shape or a basic design shape.

Such a shape is not appropriate to the wearable device and acts as a factor delimiting functions and design of the wearable device.

In addition, where the wearable device has the body and the wearing part are integrally formed with each other, the body and the wearing part are not changeable and thus there is a limitation to providing various designs and customized functions. Furthermore, if the body and the wearing part are separable from each other and changeable, it would be possible to customize the wearable device according to a user's taste in view of an exterior design or function. However, there is a contradiction between the degree of fastening and convenience in removing the body, and deterioration of the wearing part caused by an individual using pattern or frequent replacement may cause a serious problem in the fixing stability of the device.

SUMMARY

In an aspect of the present disclosure a wearable device is provided which has a body exterior configured to be easy to wear and to smoothly perform functions, and that facilitates housing electronic parts in the body of the device.

In another aspect of the present disclosure a wearable device that is easy for a user to wear on the user's wrist is provided.

Another aspect of the present disclosure may be to provide a wearable device that includes a removable body and includes a wearing part that may be changed according to a user's taste.

Another aspect of the present disclosure may be to provide a wearable device in which a place where a biometric sensor is mounted is configured to easily contact the skin of a human body, and where the biometric sensor can be used as a personal auxiliary medical device.

Another aspect of the present disclosure is to provide a wearable device, which provides coupling and decoupling directions of a body, and thus can prevent or inhibit the body from being decoupled when being worn on a wrist.

According to an aspect of the present disclosure, a wearable device may include: a strap having a first end and a second end. The strap may include a substantially polygonal opening and a buckle formed at one of the first and second ends of the strap. A buckle part may be configured to fasten the first and second ends of the strap to each other by binding the opposite ends (i.e., the first and second ends) of the strap. A body may be configured to be coupled to the opening by being fitted into the opening or decoupled from the opening. The body may include a front surface and a rear surface, and may also include a display having a substantially polygonal shape when viewed from the top, on the front surface. A biometric sensor may be disposed on the rear surface of the body.

According to another aspect of the present disclosure, a wearable device may includes: a body housing; a curved display disposed on a front surface of the body housing; a curved battery layered under the curved display; and a curved body including one or a plurality of substrates arranged between the curved battery and the rear surface of the body housing.

According to an embodiment of the present disclosure, the wearable device may include a wearing part that is changeable or replaceable (e.g., decoupled from the body) such that a user may select a wearing part according to the user's taste. Thus, the user can select a wearing part reflecting consumer's personality.

Another aspect of the present disclosure may be to provide a wearable device provided with a wearing structure that is able to respond to various wrist curvatures. For example, the a wearing part may able to respond to various wrist curvatures, thereby improving wearability. The wearable device may include a body housing, a curved display disposed on a front surface of the body housing, a curved battery layered under the curved display, and a curved body comprising at least one substrate arranged between the curved battery and the rear surface of the body housing.

According to another embodiment of the present disclosure, the wearable device may include a wearable part and a body that may be coupled or decoupled from one another by moving the wearable part and the body relative to one another in either a coupling or decoupling direction. The coupling and decoupling directions may be such that the body is inhibited from being inadvertently separated from the wrist and is stably worn on the user's wrist.

These and other aspects of the present disclosure will be more fully described with reference to the appended drawings.

BRIEF DESCRIPTION OF THE DRAWINGS

For a more complete understanding of the present disclosure and its advantages, reference is now made to the following description taken in conjunction with the accompanying drawings, in which like reference numerals represent like parts.

DETAILED DESCRIPTION

Figure 1:
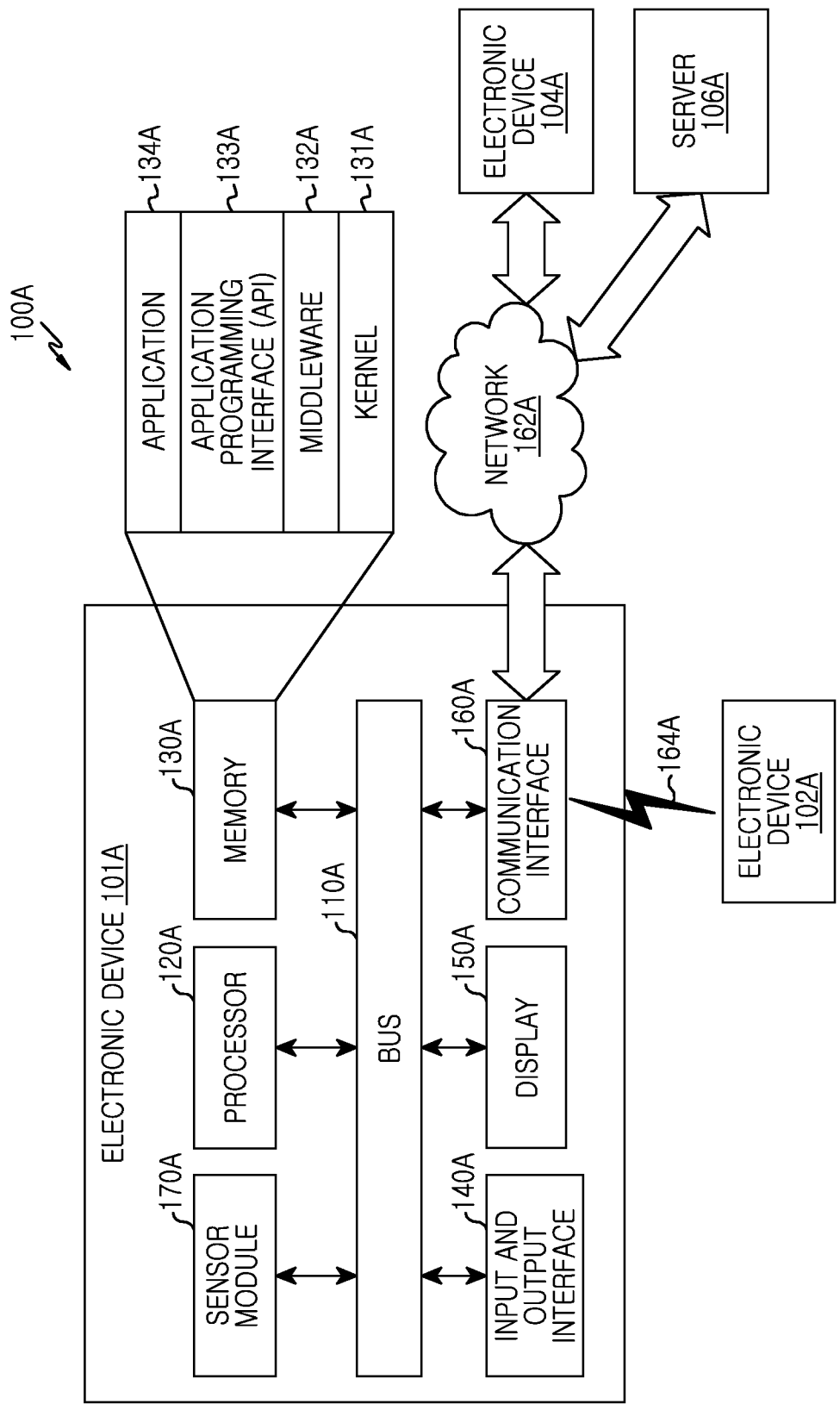
FIG. 1 is a block diagram schematically showing an inner configuration of a network environment including an electronic device.

Hereinafter, the present disclosure will be explained with reference to the accompanying drawings.

The term "substantially" used in the embodiments of present disclosure is used to imply that a cited characteristic, parameter, or value is not necessarily achieved exactly and that an allowable error, a measurement error, a limitation of measurement accuracy, a deviation or change including other elements known to a person skilled in the art, and an effect that a characteristic is to provide are not excluded.

Although specific embodiments of the present disclosure are illustrated in the drawings and relevant detailed descriptions are provided, various changes can be made and various embodiments may be provided. Accordingly, various embodiments of the present disclosure are not limited to the specific embodiments and should be construed as including all changes, equivalents or substitutes included in the ideas and technological scopes of embodiments of the present disclosure. In the explanation of the drawings, similar reference numerals are used for similar elements.

The terms "include" or "may include" used in the embodiments of the present disclosure indicate the presence of disclosed corresponding functions, operations, elements, and the like, and do not limit additional one or more functions, operations, elements, and the like. In addition, it should be understood that the terms "include" or "have"

used in the embodiments of the present disclosure are to indicate the presence of features, numbers, steps, operations, elements, parts, or a combination thereof described in the specifications, and do not preclude the presence or addition of one or more other features, numbers, steps, operations, elements, parts, or a combination thereof.

The term "or" used in the embodiments of the present disclosure includes any and all combinations of words enumerated with it. For example, "A or B" means including A, including B, or including both A and B.

Although the terms such as "first" and "second" used in the various embodiments of the present disclosure may modify various elements of the various embodiments, these terms do not limit the corresponding elements. For example, these terms do not limit an order and/or importance of the corresponding elements. These terms may be used for the purpose of distinguishing one element from another element. For example, a first user device and a second user device all indicate user devices and may indicate different user devices. For example, a first element may be named a second element without departing from the scope of right of the various embodiments of the present invention, and similarly, a second element may be named a first element.

It will be understood that when an element is mentioned as being "connected" or "coupled" to another element, the element may be directly connected or coupled to another element, and there may be an intervening element between the element and another element. To the contrary, it will be understood that when an element is mentioned as being "directly connected" or "directly coupled" to another element, there is no intervening element between the element and another element.

The terms used in the various embodiments of the present disclosure are for the purpose of describing specific embodiments only and are not intended to limit the present disclosure. As used herein, the singular forms are intended to include the plural forms as well, unless the context clearly indicates otherwise.

All of the terms used herein including technical or scientific terms have the same meanings as those generally understood by an ordinary skilled person in the related art unless they are defined otherwise. The terms defined in a generally used dictionary should be interpreted as having the same meanings as the contextual meanings of the relevant technology and should not be interpreted as having ideal or exaggerated meanings unless they are clearly defined in the various embodiments.

An electronic device according to various embodiments of the present disclosure may be a device that is equipped with a communication function. For example, the electronic device may include at least one of a smartphone, a tablet personal computer (PC), a mobile phone, a video phone, an electronic book reader, a desktop PC, a laptop PC, a netbook computer, a Personal Digital Assistant (PDA), a Portable Multimedia Player (PMP), an MP3 player, a mobile medical machine, a camera, or a wearable device (e.g., a head-mounted-device (HMD) such as electronic glasses, electronic clothing, an electronic bracelet, an electronic necklace, an electronic appcessory (e.g., an accessory (e.g., a heart monitor) configured to work with an application of the electronic device), electronic tattoos, or a smartwatch).

According to an embodiment, the electronic device may be a smart home appliance that is equipped with a communication function. For example, the smart home appliance may include at least one of a television, a Digital Video Disk (DVD) player, a stereo, a refrigerator, an air conditioner, a cleaner, an oven, a microwave oven, a washing machine, an air cleaner, a set-top box, a TV box (for example, Samsung HomeSync™, Apple TV™, or Goggle TV™), a game console, an electronic dictionary, an electronic key, a camcorder, or an electronic album.

According to an embodiment, the electronic device may include at least one of various medical machines (for example, Magnetic Resonance Angiography (MRA), Magnetic Resonance Imaging (MRI), Computerized Tomography (CT), a tomograph, an ultrasound machine, and the like), a navigation device, a Global Positioning System (GPS) receiver, an Event Data Recorder (EDR), a Flight Data Recorder (FDR), an automotive infotainment device, electronic equipment for ship (for example, a navigation equipment for ship, a gyro compass, and the like), avionics, a security device, or an industrial or home robot.

According to an embodiment, the electronic device may include at least one of a part of furniture or a building/a structure including a communication function, an electronic board, an electronic signature receiving device, a projector, and various measurement devices (for example, water, power, gas, radio waves, and the like). The electronic device according to various embodiment of the present disclosure may be one or a combination of one or more of the above-mentioned devices. In addition, it is obvious to an ordinary skilled person in the related art that the electronic device according to various embodiments of the present disclosure is not limited to the above-mentioned devices.

Hereinafter, an electronic device according to various embodiments will be explained with reference to the accompanying drawings. The term "user" used in the various embodiments may refer to a person who uses the electronic device or a device that uses the electronic device (for example, an artificial intelligence electronic device).

FIG. 1 illustrates a network environment 100A including an electronic device 101A according to various embodiments of the present disclosure. Referring to FIG. 1, the electronic device 101A may include a bus 110A, a processor 120A, a memory 130A, an input and output interface 140A, a display 150A, a communication interface 160A, and a sensor module 170A.

The bus 110A may be a circuit, which connects the above-described elements with one another and transmits communication signals (for example, a control message) between the above-described elements.

The processor 120A may receive instructions from the other elements (for example, the memory 130A, the input and output interface 140A, the display 150A, the communication interface 160A, or the sensor module 170A) via the bus 110A, decipher the instructions, and perform calculation or data processing according to the deciphered instructions.

The memory 130A may store instructions or data which is received from or generated by the processor 120A or the other elements (for example, the input and output interface 140A, the display 150A, the communication interface 160A, the sensor module 170A, and the like). For example, the memory 130A may include programming modules such as a kernel 131A, middleware 132A, an Application Programming Interface (API) 133A, an application 134A, and the like. Each of the above-described programming modules may be configured by software, firmware, hardware, or a combination of two or more of them.

The kernel 131A may control or manage system resources (for example, the bus 110A, the processor 120A, the memory 130A, and the like) which are used for performing operations or functions implemented in the other programming modules, for example, the middleware 132A, the API 133A, or the application 134A. In addition, the kernel 131A may provide an interface for allowing the middleware 132A, the API 133A, or the application 134A to access an individual element of the electronic device 101A and control or manage the element.

The middleware 132A may serve as an intermediary to allow the API 133A or the application 134A to communicate with the kernel 131A and exchange data with the kernel 131A. In addition, the middleware 132A may perform controlling (for example, scheduling or load balancing) with respect to work requests received from the application 134A, for example, by giving priority to use the system resources of the electronic device 101 (for example, the bus 110A, the processor 120A, the memory 130A, and the like) to at least one of the applications 134A.

The API 133A may be an interface for allowing the application 134A to control a function provided by the kernel 131A or the middleware 134A, and, for example, may include at least one interface or function (for example, instructions) for controlling a file, controlling a window, processing an image, and/or controlling a text.

According to various embodiments, the application 134A may include a Short Message Service (SMS)/Multimedia Messaging Service (MMS) application, an email application, a calendar application, a notification application, a health care application (for example, an application for measuring exercise or a blood sugar), an environment information application (for example, an application for providing information on atmospheric pressure, humidity, or temperature), and the like. Additionally or alternatively, the application 134A may be an application related to information exchange between the electronic device 101A and an external electronic device (for example, an electronic device 102A or an electronic device 104A). For example, the application related to the information exchange may include a notification relay application for relaying specific information to the external electronic device or a device management application for managing the external electronic device.

For example, the notification relay application may include a function of relaying notification information generated by other applications of the electronic device 101A (for example, the SMS/MMS application, the email application, the health care application, the environment information application, and the like) to the external electronic device (for example, the electronic device 102A or the electronic device 104A). Additionally or alternatively, the notification relay application may receive notification information from the external electronic device (for example, the electronic device 102A or the electronic device 104A) and may provide the same to the user. For example, the device management application may manage (for example, install, delete or update) a function regarding at least part of the external electronic device (e.g., the electronic device 102A or the electronic device 104A) communicating with the electronic device 101A (for example, turning on/off the external electronic device (or some parts) or adjusting brightness of a display), an application operating in the external electronic device or a service provided by the external electronic device (e.g.: a calling service or a message service).

According to various embodiments, the application 134A may include an application specified according to an attribute (for example, a kind of an electronic device) of the external electronic device (for example, the electronic device 102A or the electronic device 104A). For example, when the external electronic device is an MP3 player, the application 134A may include an application related to music replay. Similarly, when the external electronic device is a mobile medical device, the application 134A may include an application related to health care. According to an embodiment, the application 134A may include at least one of an application specified by the electronic device 101A or an application received from the external electronic device (for example, a server 106A, the electronic device 102A, or the electronic device 104A).

The input and output interface 140A may transmit instructions or data input by a user through a sensor (for example, an acceleration sensor or a gyro sensor) or an input device (for example, a keyboard or a touch screen) to the processor 120A, the memory 130A, or the communication interface 160A through the bus 110A, for example. For example, the input and output interface 140A may provide data on a user's touch input through a touch screen to the processor 120A. In addition, the input and output interface 140A may output instructions or data received from the processor 120A, the memory 130A, the communication interface 160A, or the sensor module 170A through the bus 110A through an output device (for example, a speaker or a display). For example, the input and output interface 140A may output voice data processed through the processor 120A to the user through a speaker.

The display 150 may display a variety of information (for example, multimedia data, text data, and the like) for the user.

The communication interface 160A may connect communication between the electronic device 101A and the external device (for example, the electronic device 102A, the electronic device 104A, or the server 106A). For example, the communication interface 160A may support network communication 162A (for example, the Internet, a Local Area Network (LAN), A Wire Area Network (WAN), a telecommunication network, a cellular network, a satellite network, a Plain Old Telephone Service (POTS), and the like), and short-distance communication 164A (for example, Wireless Fidelity (WiFi), Bluetooth (BT), Near Field Communication (NFC), or wired communication (for example, a Universal Serial Bus (USB), a High Definition Multimedia Interface (HDMI), a Recommended Standard 232 (RS-232), or POTS)). According to an embodiment, a protocol for communicating between the electronic device 101A and the external device (for example, a short-distance communication protocol, a network communication protocol, or a wired communication protocol) may be supported in at least one of the API 133A or the middleware 132A. The electronic device 102A, 104A may be the same device as the electronic device 101A (for example, the same type of device) or a different device (for example, a different type of device).

The sensor module 170A may measure a physical quantity or detect an operation state of the electronic device, and may convert measured or detected information into electric signals. The sensor module 170A may include at least one of a gesture sensor, a gyro sensor, a barometric pressure sensor, a magnetic sensor, an acceleration sensor, a grip sensor, a proximity sensor, a color sensor (for example, Red, Green, Blue (RGB) sensor), a biosensor, a temperature/humidity sensor, an illumination sensor, and a Ultraviolet (UV) sensor.

Additionally or alternatively, the sensor module 170A may include an E-nose sensor, an electromyography (EMG) sensor, an electroencephalogram (EEG) sensor (not shown), an electrocardiogram (ECG) sensor (not shown), an infrared ray (IR) sensor, an iris sensor (not shown), a fingerprint sensor, and the like.

Figure 2:
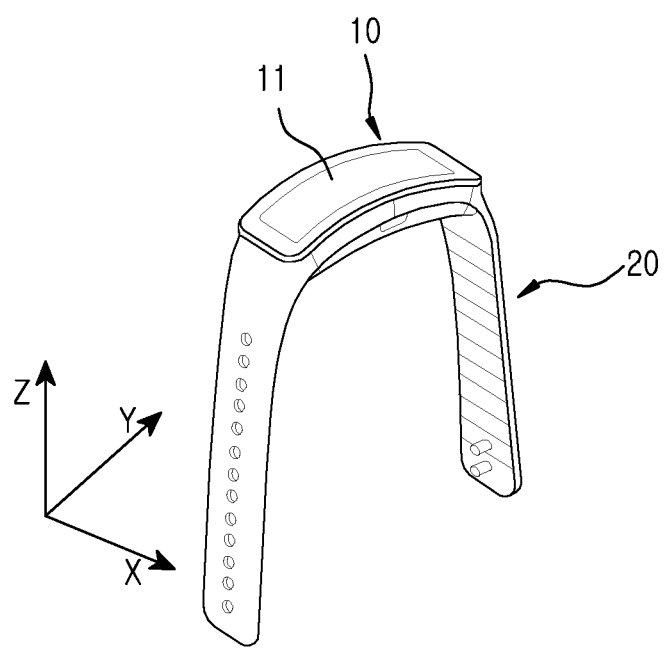
FIG. 2 is a perspective view showing a wearable electronic device including a wearable part and a curved body according to an embodiment of the present disclosure.
Figure 3:
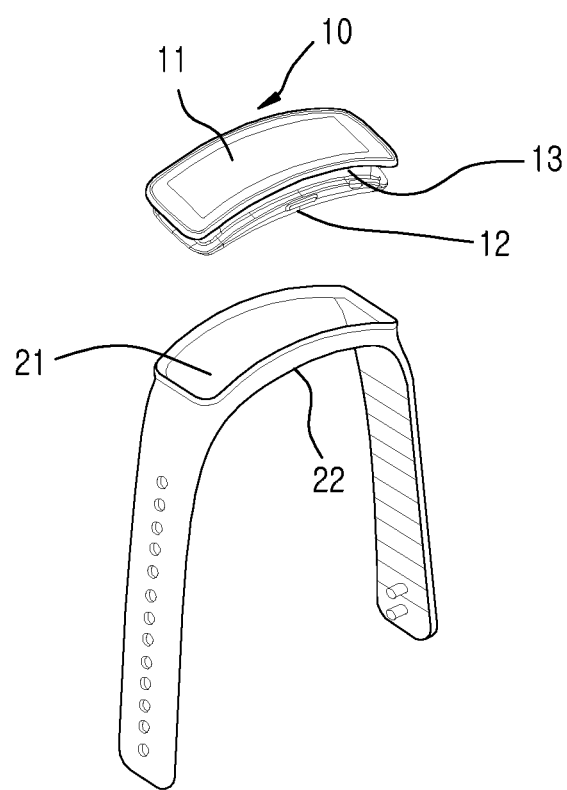
FIG. 3 is a perspective view showing the wearable electronic device of FIG. 2 in which the body and the wearing part are separated from each other.

FIG. 2 is a perspective view showing a wearable device according to various embodiments of the present disclosure. FIG. 3 is a perspective view showing a wearable device in which a curved body 10 and a wearing part 20 are separated from each other according to various embodiments of the present disclosure.

Referring to FIGS. 2 and 3, a 3-dimensional X/Y/Z orthogonal coordinate system is illustrated. "Z-axis" is a vertical direction and means an up and down direction (thickness direction) of the body 10, "X-axis" is a first horizontal direction and means a widthwise direction of the body 10, and "Y-axis" is a second horizontal direction perpendicular to the first horizontal direction and means a lengthwise direction of the body 10.

The wearable device according to various embodiments of the present disclosure is a user device, which is worn on a human body, and may be an electronic device that is relatively easy to wear on a wrist like a watch or bracelet, a communication device, or an auxiliary medical device. However, the wearable device according to various embodiments of the present disclosure is not limited to the device that is worn on a wrist. For example, the wearable device according to various embodiments of the present disclosure can be equally applied to any part of the human body where a curvature exists. For example, examples of a part of the human body where a curvature exists may be a wrist, an arm, an ankle, or the like. In addition, the wearable device according to various embodiments of the present disclosure can be stably worn on various parts of the body when the wearing part 20 is configured in various ways.

The wearable device according to various embodiments of the present invention may include the body 10 (function device part) and the wearing part 20 (including a band or strap). The body 10 may be configured to be forcibly coupled to or decoupled from the wearing part 20. The body 10 may include a display 11 for externally displaying a variety of information, and a press key (e.g., a side key) (k), a sensor (s), a touch input part, and the like for inputting a variety of information. The body 10 may formed in a bar shape and may also have a curvature. Specifically, the body 10 may have a shape extending in the lengthwise direction (Y-axis direction) and may have a curvature.

The wearing part 20 may be made of an elastic material and allows the body 10 to be worn on a human body stably and brings the body 10 into close contact with the skin of the human body. In addition, since the wearing part 20 is changeable, the wearing part 20 may function as an accessory reflecting user's personality or taste. However, a part (seating part) of the wearing part 20, which is coupled to the body 10, may be configured to be elastically deformable and a wearing surface part, which is in close contact with the human body, may not be made of an elastic material. The wearing part 20 may be provided with an opening 21 which is opened in the up and down directions, and may includes a seating part 22 which is elastically deformable along a circumference of the opening 21. The wearing part 20 includes an elastic member (seating part) at least around the opening 21, and, when the body 10 is coupled to the wearing part 20, at least part of the seating part including the elastic member may be fitted into or mated with a seating recess which extends along a side surface of the body 10.

The opening 21 is an open space into which the body 10 is fitted and has a shape enclosed by the seating part 22. The opening 21 according to the present embodiment may be formed in a substantially rectangular shape having a thickness. The opening 21 may have a substantially rectangular shape when viewed from the top, having the side in a first direction longer than the side in the direction perpendicular to the first direction. In addition, the opening 21 includes at least one linear portion enclosing the opening 21. Two linear portions may be provided and configured in parallel with each other, facing each other. The wearing part 20 may include a buckle part for fastening both ends of the wearing part 20 by binding the ends. The wearing part 20 may be configured to include a band extending in the first direction (Y-axis direction). The band includes an opening formed on a part thereof, and includes a buckle part formed at one end thereof and a fastening part formed at the other end to be removably fastened to the buckle part. In addition, the curved display 11 may be configured to have a substantially rectangular shape smaller than the opening 21, when viewed from the top.

In addition, the wearable device according to embodiments of the present disclosure may include a removable structure which enables the body 10 to be mechanically coupled/decoupled, and the removable structure includes a seating recess 13 provided on the body 10, and the opening 21 and the seating part 22 provided on the wearing part 20.

The wearable device may include the seating recess 13 formed along the circumference of the side surface of the surfaces of a body housing, and the seating part 22 formed on the wearing part 20 to be fitted into the seating recess 13. After the body 10 is fitted into the seating part 22, the body 10 can be more securely fixed to the wearing part 20 by other means (not shown).

The body 10 may be curved and hereinafter is referred to as a curved body. However, it is to be understood that the body 10 is not limited to a curved configuration and may instead, for example, be generally planar, flat, and/or rectangular. The curved body 10 will be explained in detail below. The seating part 22 is made of an elastic material and may be elastically deformable, the curved body 10 is removable from the seating part 22. In addition, due to the shape of the curved body 10 and the removable structure, the body 10 may be forcedly coupled to or decoupled from the wearing part 20 with directions.

The wearing part 20 may be changeable, and may be changed according to a user's taste when the wearing part 20. The wearing part 20 may be implemented in various designs or colors such that the wearing part 20 may be regarded as an accessory reflecting the user's own personality and tastes.

Figure 4:
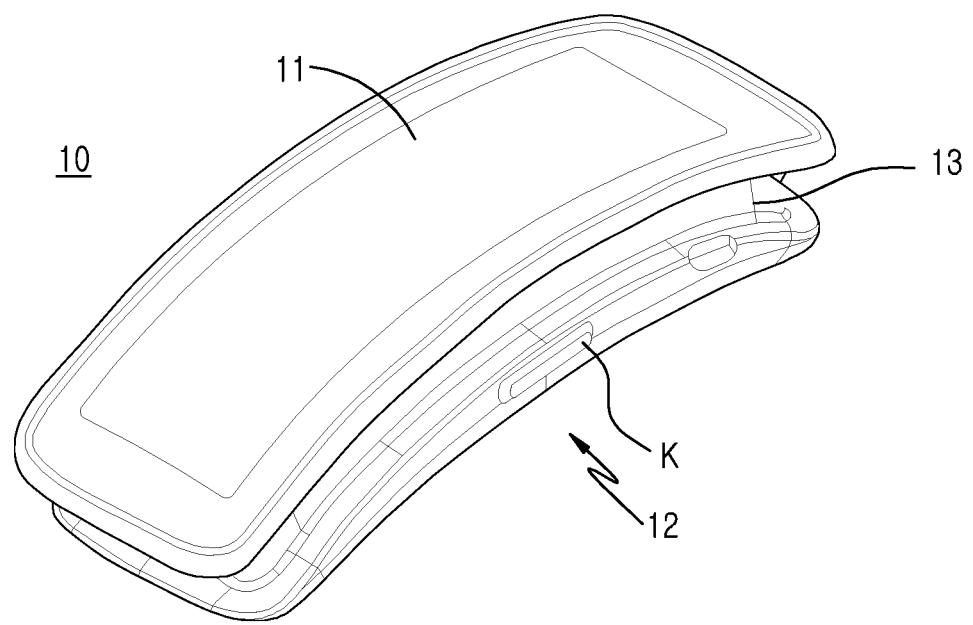
FIG. 4 is a perspective view showing a front surface of the curved body of FIG. 2.
Figure 5:
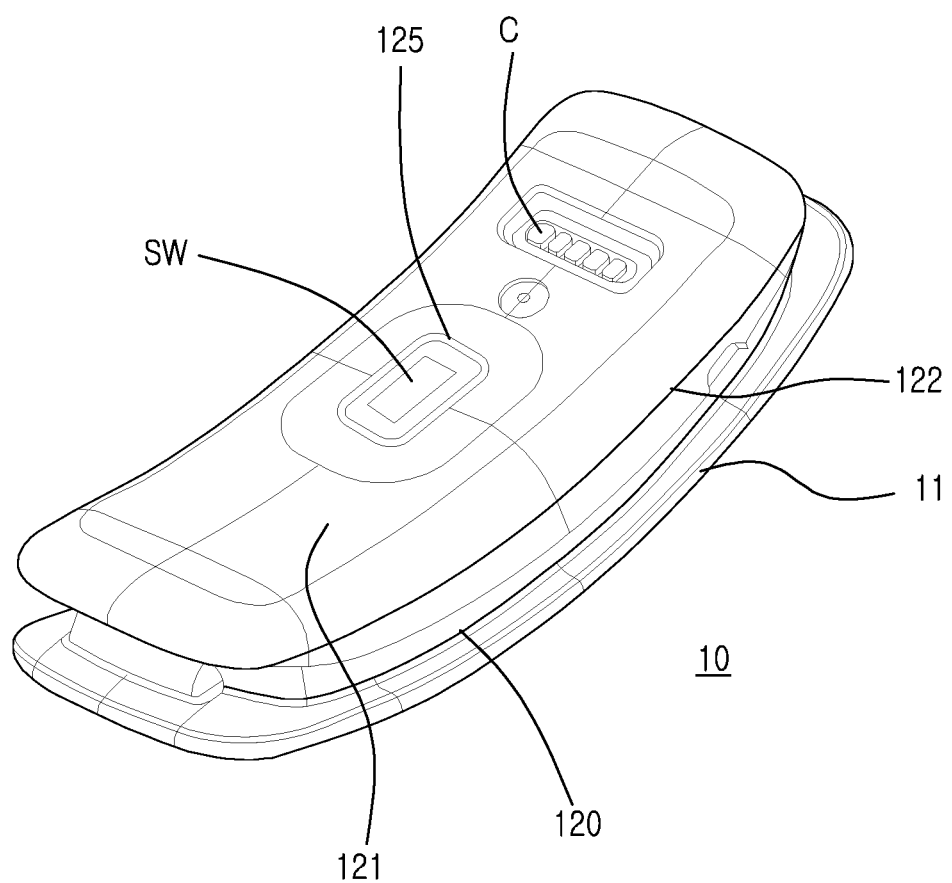
FIG. 5 is a perspective view showing a rear surface of the body of FIG. 2.
Figure 6:
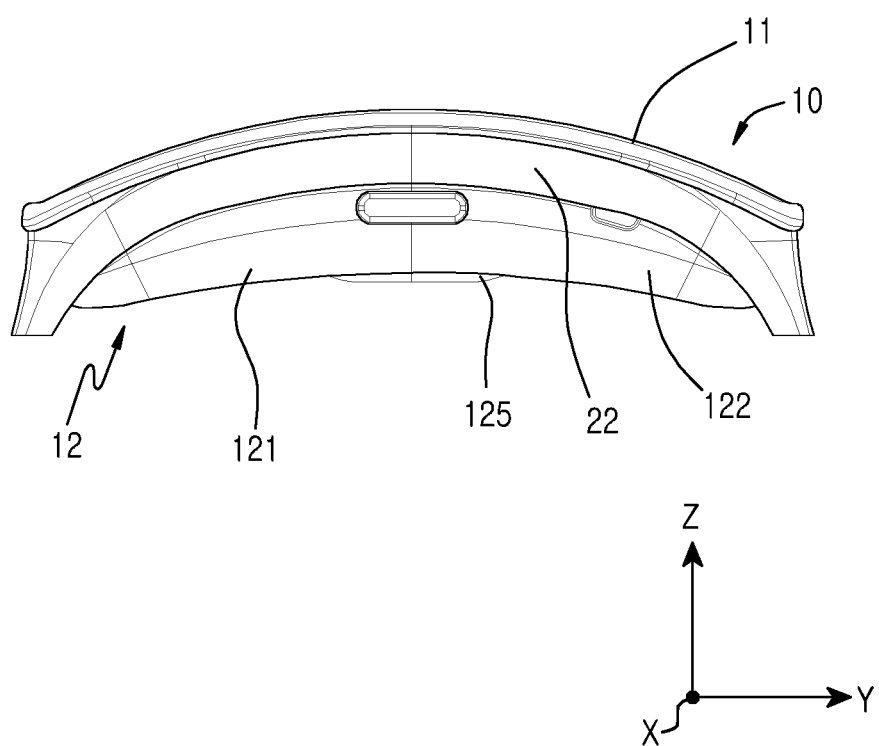
FIG. 6 illustrates a side view of the body of FIG. 2.

FIG. 4 is a perspective view showing a front surface 120 of the curved body 10 according to various embodiments of the present disclosure. FIG. 5 is a perspective view showing a rear surface 121 of the curved body 10 according to various embodiments of the present disclosure. FIG. 6 is a side view showing the curved body 10, which is coupled to the seating part of the wearing part 20, according to various embodiments of the present disclosure. The exterior configuration of the curved body 10 will be explained in detail with reference to FIGS. 4 to 6.

The curved body 10 according to various embodiments of the present disclosure is formed in a bar shape such as a rectangular shape, extends in a curved direction, and has an elongated shape, while having a curvature. The curved body 10 may include a body housing 12 and a display 11, which may be mounted in the body housing 12. The body housing 12 includes a front surface 120, a rear surface 121, and a side surface 122, and the front surface 120 and the rear surface 121 each has a curvature. The front surface 120 is a surface where the display 11 is mounted, and the rear surface 121 is a wearing surface which is in contact with a human body. The front surface 120 has a first curvature and the rear surface 121 has a second curvature. The first and second curvatures may be determined to facilitate improved consumer wearability by having a shape or configuration to ergonomically correspond to various consumers' wrists. In the present embodiment, the first curvature is smaller than the second curvature. In other words, the front surface 120 of the curved body 10 according to the present embodiment has the display 11 mounted therein and thus should make it easy for a user to view a displayed screen, and the rear surface 121 should make the user feel good when the user wears the device on user's wrist, and has a sensor mounted thereon and thus should provide a shape closely contacting user's wrist.

The curved body 10 may be configured to gradually become thinner from the center toward the opposite sides thereof. The curved body 10 may be relatively thick on the center and may gradually become thinner toward the sides. In addition, although the rear surface 121 has the second curvature in the above-described embodiment, the rear surface 121 may be a substantially flat surface without a curvature.

The exterior structure of the curved body 10 can ergonomically improve a sensation that a user may feel when wearing the device and can improve compatibility in response to various consumers' wrists. The curved body 10 may be provided with the curved display 11 on the front surface 120 and may include a skin contact surface provided with a sensor 13 (an interface of the sensor is seen in FIG. 4) on the rear surface 121, so that the degree of freedom of the exterior design can be maximized and optimal sensor performance can be provided to all of the users. In particular, the rear surface 121 of the curved body 10, which is the skin contact surface, may be configured as a nearly flat surface in comparison to the free shape of the exterior design of the curved body 10, and may have the sensor (s) arranged thereon to respond to all of the various body curvatures appropriately.

In addition, the curved body housing 12 in the present embodiment may have a sensor interface (SW) formed on the rear surface thereof which is in close contact with user's skin, and has the display, a touch input part, a button key, a charging terminal, and an information interface formed on a surface other than the skin contact surface (bottom surface of the body housing).

The display 11 is formed in a shape reflecting a curved shape of the human body and may be formed in a flat shape (Liquid Crystal Display (LCD), Organic Light Emitting Diode (OLED)) or a curved shape (flexible OLED). Although the display 11 is provided in the present embodiment is described as being curved, the display 11 may instead be configured as a flat display.

A seating recess 13 may be formed on the side surface of the curved body housing 12. The seating recess 13 extends along the side surface 122 of the curved body housing 12. An exterior side surface of the side surfaces of the curved body housing 12 that is seen by the user has a curvature. The seating recess 13 has the same curvature as the first curvature of the front surface 120 of the curved body housing 12. However, the curvature of the seating recess 13 may be the same as the first curvature, but may be larger or smaller than the first curvature since men and woman have various wrist curvatures. In FIG. 6, the curvature of the seating recess 13 is the same as the first curvature. As will be described, the seating recess 13 includes a top surface curvature and a bottom surface curvature in some section. The bottom surface curvature may vary to respond to various wrist curvatures. The top surface curvature and the bottom surface curvature of the seating recess 13 may vary in a boundary area with the body according to a wrist curvature of a user who wears the wearable device.

In the above-described embodiment, the seating recess 13 has a curvature, and a top surface 33a and a bottom surface 33b of the seating recess 13 have the same curvature. The seating recess 13 formed on the outside surface of the body housing 12 may extend to have the curvature with the same width and the same thickness and thus the top surface 33a and the bottom surface 33b of the seating recess 13 have the same curvature as the first curvature.

Figure 7:
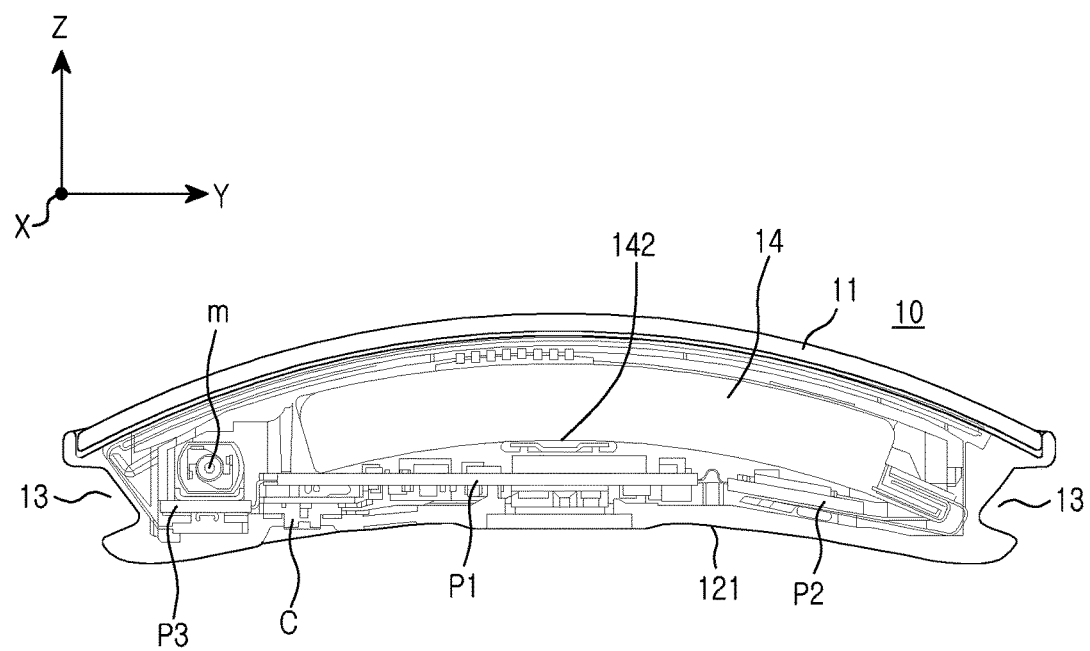
FIG. 7 is a side cross-sectional view of the body of FIG. 2.
Figure 8:
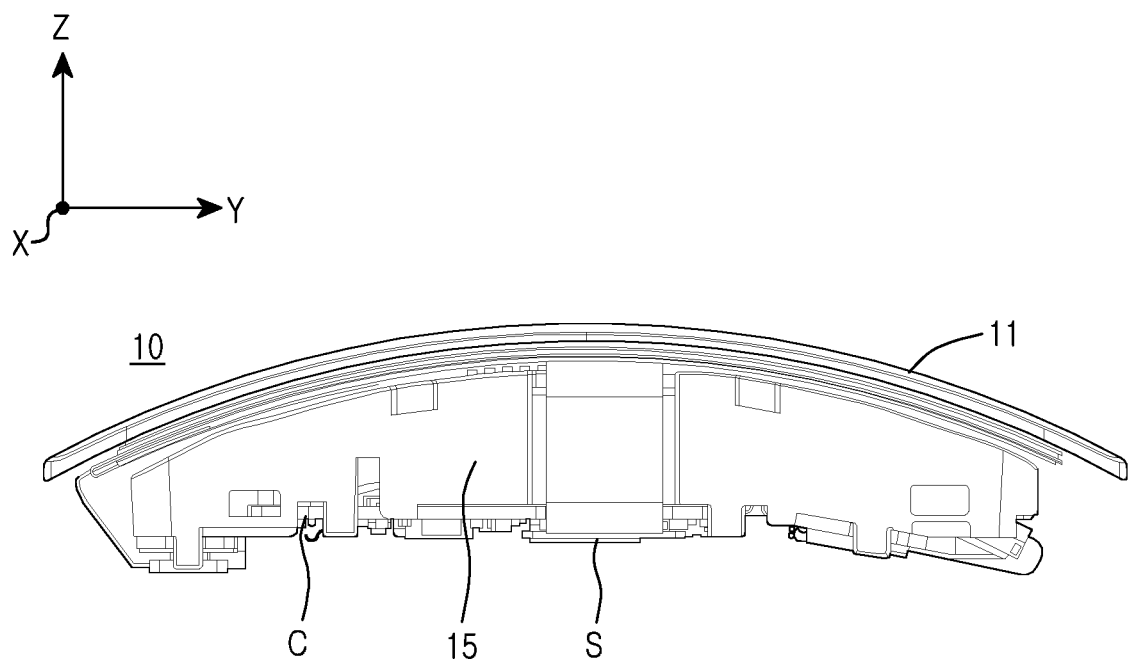
FIG. 8 is a side cross-sectional view of the body of FIG. 2 showing an inner bracket and a display, which are coupled to each other according to various embodiments of the present disclosure.
Figure 9:
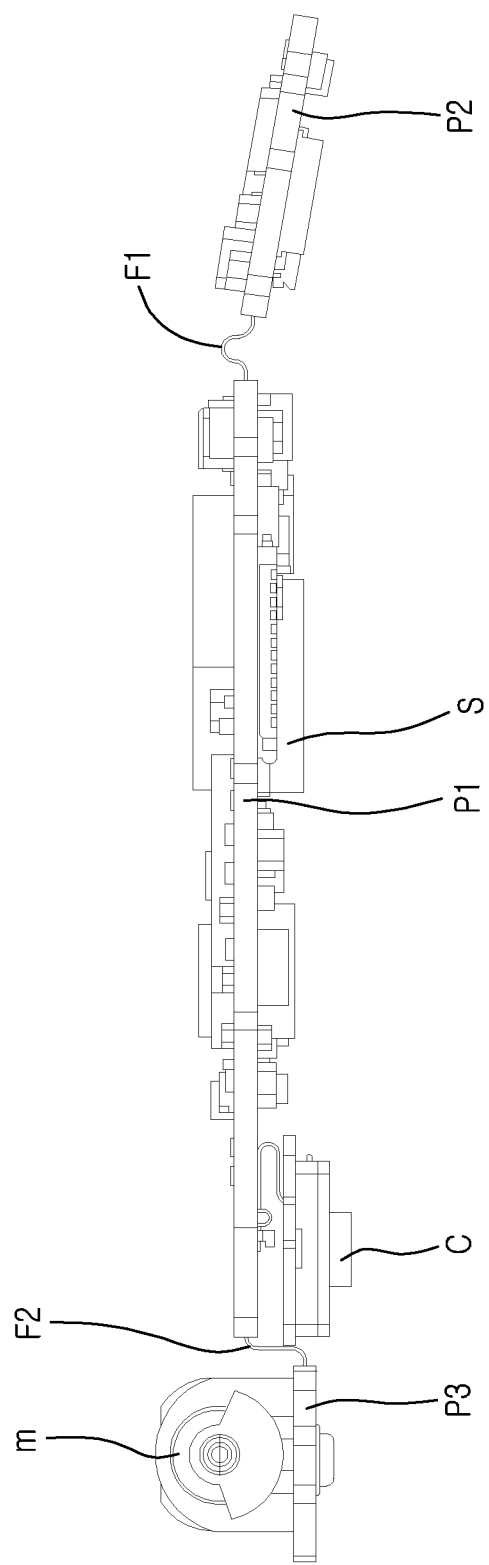
FIG. 9 illustrates a side view of the body of FIG. 2 with parts removed.

FIG. 7 is a section view showing arrangement of electronic parts provided in the curved body 10 according to various embodiments of the present disclosure. FIG. 8 is a side view showing the curved body 10 according to various embodiments of the present disclosure. FIG. 9 is a side view showing arrangement of substrates and electronic parts provided in the curved body 10 according to various embodiments of the present disclosure.

Arrangement of electronic parts mounted in the curved body 10 will be explained with reference to FIGS. 7 to 9. In the present embodiment, a curved battery 14 is mounted under the display 11 in a layered structure, such that the curved body 10 gradually becomes thinner from the center toward the opposite sides. That is, the curved body 10 has the curved display 11, the curved battery 14, and substrates P1-P3 layered therein one on another.

In the present embodiment, the curved body 10 may be configured such that an exterior surface which is easily seen with user's eyes (for example, a display screen) and a contact surface which is worn on a human body and is in close contact with a skin (a rear surface of the body housing) have different curvatures, and has an optimum layered structure of electronic parts mounted therein. The curved body 10 according to the present embodiment is provided with the display 11 having the highest degree of freedom of manufacturing a curved surface on the exterior surface having the largest curvature, and has the battery 14 installed inside the display 11. In this case, the battery 14 has a curved shape and has the same curvature as the first curvature. The battery 14 may be mounted with reference to the center of the curved display 11, and facilitates providing or guaranteeing mounting spaces that are formed at both ends of the battery. The mounting spaces may be used as spaces for compensating for reduction in the curvature of the skin contact surface (rear surface). The above-described mounting structure results in reduction in the thickness at the both ends in comparison to the center of the curved body 10, thereby achieving a good design and minimizing a step height which may be generated with respect to the wearing part 20.

Hereinafter, the arrangement of various electronic parts and substrates mounted in the curved body 10 will be explained.

The curved battery 14, a plurality of electronic parts s, m, and c and a plurality of substrates P1, P2, and P3 are arranged in the curved body 10. The curved display 11, the curved battery 14, and the plurality of substrates P1, P2, and P3 are arranged in the curved body 10 in a vertically layered structure. In particular, the battery 14 according to the present embodiment is disposed on an intermediate layer between the curved display 11 and the substrate P1. This structure is to serve as a safety device for preventing a low temperature burn caused by heat emitted from the battery and minimizing any damage to the user caused by explosion of the battery, and may be a vertically layered structure.

The curved body 10 includes the curved body housing 12 and an inner bracket 15. The curved body 10 forms a single body by coupling the inner bracket 15 to the curved body housing 12. The body housing 12 and the inner bracket 15 may be independently manufactured and coupled to each other. However, the inner bracket 15 may be included in the body housing 12. The curved display 11 may be attached to the front surface of the body housing 12 by an adhesive tape (double-sided waterproof tape), and the inner bracket 15 may be received in and fixed to the body housing 12. The inner bracket 15 may receive the curved battery which is layered under the curved display 11 and one or the plurality of substrates P1, P2, and P4 arranged between the front surface 120 and the rear surface 121 of the body housing 12.

In addition, according to the present embodiment, the plurality of substrates P1, P2, and P4 may be arranged in the inner space of the body housing 12, specifically, in the inner bracket 15. In this case, a segmental (articular) structure substrate may be applied, thereby improving efficiency of mounting of the electronic parts. The above-mentioned segmental structure substrate appropriately provides rigid substrates P1, P2, and P3 and flexible substrates F1 and F2 to sections where the substrates are needed, thereby smoothly implementing a curved design, and may have the electronic parts directly arranged in respective segmental sections separately according to a required condition, thereby improving performance of the electronic device. For example, a part vulnerable to a noise and a noise generating part may be arranged on separate substrates and a part vulnerable to a shock and a shock generating part may be arranged on separate substrates. Such arrangement of the electronic parts may naturally separate a noise generating section and a noise sensitive section from each other and may block a vibration shock transmitted through the rigid substrates P1, P2, and P3 in the section of the flexible substrates F1 and F2, thereby achieving a design for optimizing electrical performance of the electronic device and durability. In the future, a curved rigid or flexible substrate will be applicable instead of the above-described rigid substrate thanks to the technology development. In the above-described substrate segmental structure, a non-contact sensor such as a gyro sensor, an acceleration sensor, and/or other optical sensors may be further provided in addition to the basic parts related to communication or input and output.

The plurality of substrates may include the plurality of rigid substrates (for example, Printed Circuit Boards (PCBs)) and the plurality of flexible substrates (PCBs), and the rigid substrates P1, P2, and P3 are substrates where various electronic parts are mounted and the electronic parts may be mounted on both the top surface and the bottom surface of each of the rigid substrates P1, P2, and P3. In FIG. 7, three rigid substrates are mounted and are referred to as a first substrate P1, a second substrate P2, and a third substrate P3. The first substrate P1 is disposed in the center, the second substrate P2 is disposed on the right of the first substrate P1, and the third substrate P3 is disposed on the left of the first substrate P1. A substrate connecting the first substrate P1 and the second substrate P2 is referred to as a first flexible substrate F1, and a substrate connecting the first substrate P1 and the third substrate P3 is referred to as a second flexible substrate F2. The first, second, and third substrates P1, P2, and P3 and the first and second flexible substrates F1 and F2 are connected with one another, thereby configuring the segmental substrate.

In addition, when various electronic parts are arranged on the first, second, and third substrates P1, P2, and P3, parts vulnerable to a noise and noise generating parts may be arranged on separate substrates, and parts vulnerable to a shock and shock generating parts may be arranged on separate substrates.

For example, out of the electronic parts mounted on the substrates, a part vulnerable to a noise (PAM) and a noise generating part (AP, CP) may be separately arranged on the first and second rigid substrates P1 and P2, respectively, and a part vulnerable to a shock (a BGA part such as AP and CP) and a shock generating part (for example, a vibrator or a vibration motor) may be separately mounted on the second and third substrates P2 and P3, respectively. Such inner arrangement of the electronic parts can naturally separate a noise generating section and a noise sensitive section from each other, and block a vibration shock transmitted through the rigid substrates in the flexible substrate section, thereby achieving a design for optimizing electrical performance of the electronic device and durability.

In addition, at least one of the rigid substrates disposed on the rear surface 121 of the body housing 12 may be horizontally placed or may be slantingly placed. The first substrate P1 is disposed in the center and has a first sensor (s) (which is exposed from the rear surface of the body housing and is in close contact with a skin of a human body to acquire a variety of information on the human body) disposed thereon. Therefore, the first substrate P1 should be placed horizontally along with the first sensor (s). The first sensor (s) may be exposed from the rear surface of the body housing and may be disposed on a location where the first sensor (s) is in the closest contact with the skin. That is, the first sensor (s) may be horizontally disposed substantially on the center of the rear surface 121 of the body housing. The first sensor (s) may be mounted on the rear surface of the first substrate P1 and a sensor interface (sensor interface window) may further be provided. In addition, even when a PCB is mounted slantingly with respect to the exterior surface of the housing, a balance can be maintained by using an interposer between the PCB and the first sensor. The first sensor (s) may have the sensor interface window exposed from the rear surface 121 of the body and may be horizontally disposed. The sensor interface window may be provided on the sensor or may be attached to the exterior of the body housing. For example, the first sensor (s) may be a Heart Rate Monitor (HRM) or a vein sensor which can acquire information from user's skin or body.

Additionally, the first sensor (s) which is exposed from the rear surface 121 of the body housing may further include a protrusion 125 protruding toward the rear surface, while enclosing the circumference of the first sensor (s) with a predetermined thickness. The protrusion 125 may make the sensor interface, for example, the sensor interface window (SW), exposed and more brought into close contact with the skin. The sensor interface (SW) is located on a flat surface of the rear surface 121 and the flat surface is located on the center.

In the present embodiment, even when the segmental structure substrates are used, at least a horizontal and flat part seating plane part (an area where the first substrate is mounted in the body housing) should be provided to mount electronic parts, and the plane part requires a plane seating structure for performing a function such as a function of a sensor. In the present embodiment, when a space guaranteed at the both ends of the curved battery 14 is used as a mounting area, a loss in the mounting space caused by the substrate being mounted on the plane can be offset. In particular, when a relatively thick part such as a vibrator (m) or a connector is placed, an inevitable increase in the total thickness of the curved body can be prevented. Although not shown, various mechanism configurations such as a sub battery or a hook assembly can be mounted in the guaranteed space.

In the curved body 10 according to the present embodiment, the third substrate P3 is disposed between the lower side of the display 11 and one side area of the battery 14 (Y-axis direction), and the motor (m) is disposed on the third substrate P3 and the charging terminal (c) is disposed on the first substrate P1. The motor (m) is horizontally disposed in parallel with the battery 14 and the charging terminal (c) is horizontally disposed in parallel with the battery 14. The motor (m) is disposed on the top surface of the third substrate P3 and the charging terminal (c) is disposed on the bottom surface of the first substrate P1. The charging terminal (c) is exposed from the rear surface 121 of the body housing. Since the motor (m) is a relatively thick part or a part of a great volume, it is advantageous to dispose the motor (m) on the second substrate P2 or the third substrate P3 in view of the efficiency of mounting.

As other input devices mounted in the substrates, an electric switch interface using a touch sensor, a pressure sensor, a temperature sensor, and the like, and a physical switch interface such as a tact dome key may be disposed on one surface of the body housing, on which the user can manipulate. Charging and interface terminals may further be disposed on a location of the front surface or the rear surface of the body housing that does not deface the exterior. In the present embodiment, the charging terminal (c) is disposed on the rear surface 121 of the body housing. According to the present embodiment, the surface that does not deface the exterior of the wearable device may be the rear surface of the body housing, that is, the surface which is in contact with the human body.

Hereinafter, the configuration of the display 11 disposed on the front surface of the curved body 10 will be explained.

Figure 10:
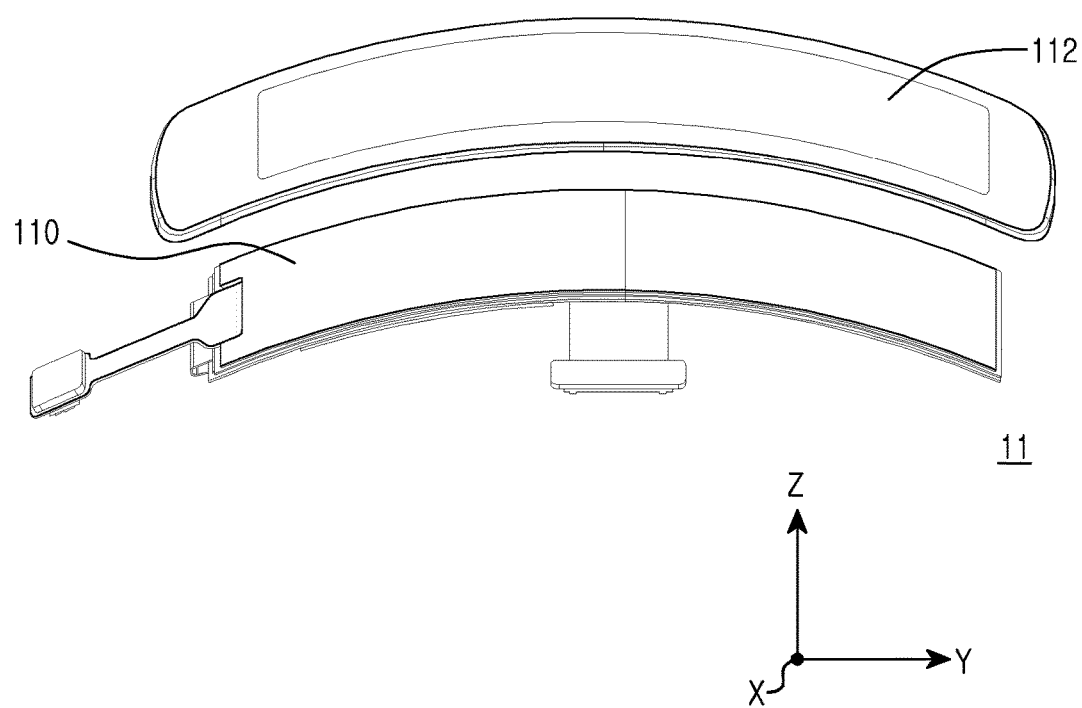
FIG. 10 is an exploded perspective view of a curved display according to an embodiment of the present disclosure.

FIG. 10 is an exploded perspective view showing the configuration of the curved display 11 provided in the curved body according to various embodiments. Referring to FIG. 10, the display 11 applies a flexible LCD 110 having a curvature and a curved window 112 having the same curvature as that of the flexible LCD 110 to achieve a curved design having a curvature. The curved window 112 includes a rigid or flexible layer.

The display 11 has a shape reflecting a curved part of a human body and may include a curved LCD (flexible OLED). The design of the front surface of the body can be achieved by the curved surface of the LCD or the curved window 112 presenting a curved surface. The display 111 may further include a sensor for detecting a touch, pressure, or temperature in addition to the curved flexible LCD 110, thereby providing a Perceptual User Interface (PUI) optimized to use of various user interface (UIs). In addition, the window 112 ma provide a layer made of a ceramic material such as glass and a sheet material such as PET, PC, and the like to protect the surface.

Figure 11:
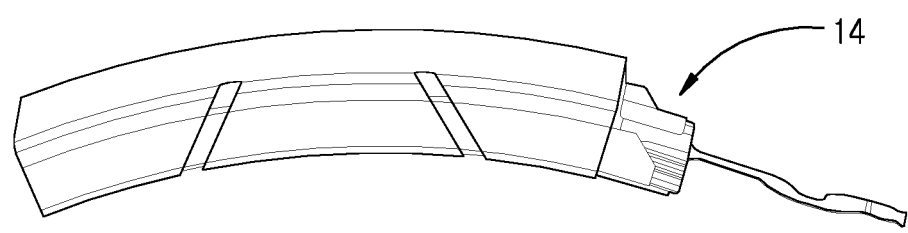
FIG. 11 illustrates a perspective view of a curved battery according to an embodiment of the present disclosure.

FIG. 11 is a perspective view showing the curved battery 14 provided in the curved body according to various embodiments of the present disclosure. Referring to FIG. 11, the battery 14 according to an embodiment of the present disclosure applies a curved battery pack, thereby improving efficiency of mounting of the electronic parts in the body. The curved battery 14 may be mounted in a bent state. This is a factor that is optimized to realize the exterior design of the curved body and mount an HW part of the wearable electronic device worn on the human body.

The battery 14 may be manufactured in a bent shape and configured to have a predetermined curvature. The front surface and the rear surface of the battery 14 each have a curvature. The curvature of the battery 14 may be the same as the curvature of the display and thus the battery 14 may be disposed to face the rear surface of the display. A mounting space may be formed on the center of the rear surface of the battery 14 and can be utilized effectively by mounting a hardware electronic part therein. The battery 14 may not have the same curvature as that of the display. In addition, although the battery 14 may be disposed between the display and the substrate, the battery 14 may be configured in a flat shape and may be disposed on the bottom surface of the substrate.

Referring back to FIG. 7, a separate layer part 142 may be added between the curved battery 14 and the first substrate P1 to prevent breakage of parts of the first substrate P1 and the battery caused by volume expansion of the curved battery 14. The layer part 142 stops volume expansion of the battery 14. The layer part 142 may act as a physical support structure or a buffering section for the curved battery 14 and the first substrate P1, and may be provided in the form of a barrier for preventing a battery liquid from leaking to the lower side. The layer part 142 may be provided as a conductive or metal piece or an injection molding piece.

Figure 12:
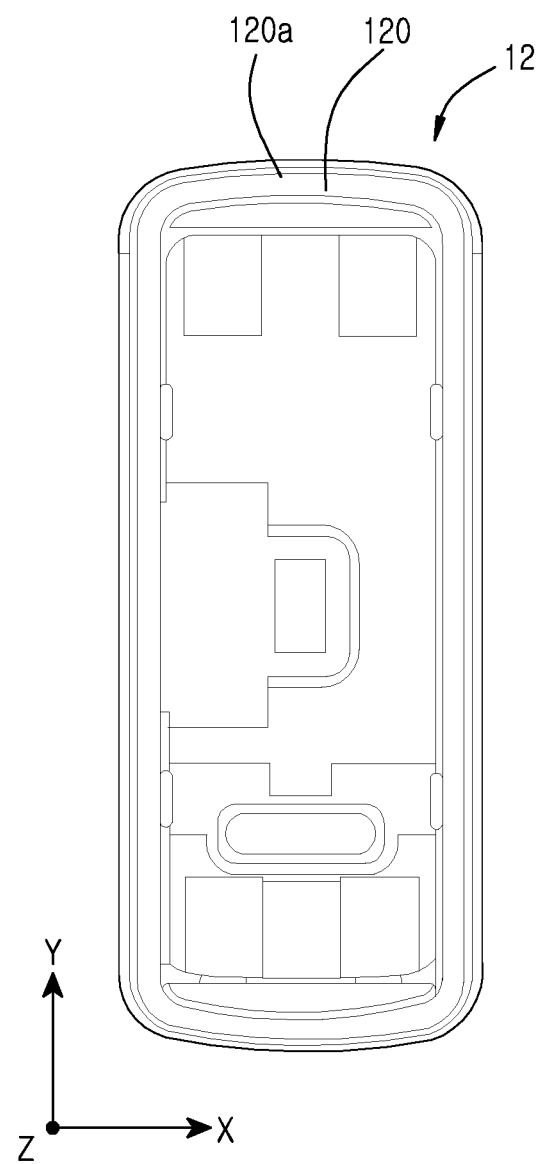
FIG. 12 is a plan view showing a front surface of a body housing according to an embodiment of the present disclosure.

FIG. 12 is a plan view showing the front surface 120 of the body housing according to an embodiment of the present disclosure. In the present embodiment, an assembly structure of the body housing 12 without a screw boss is provided. The inner bracket in which electronic parts are modularized and the body housing 12 may be fixed by a hook and the display window and the front surface 120 of the body housing may be assembled with each other by using a waterproof tape. Therefore, the inner mounting space can be maximized and the waterproof function can be maximized by excluding a screw boss. Reference numeral 120a indicates a surface to which the waterproof tape is attached.

Figure 13:
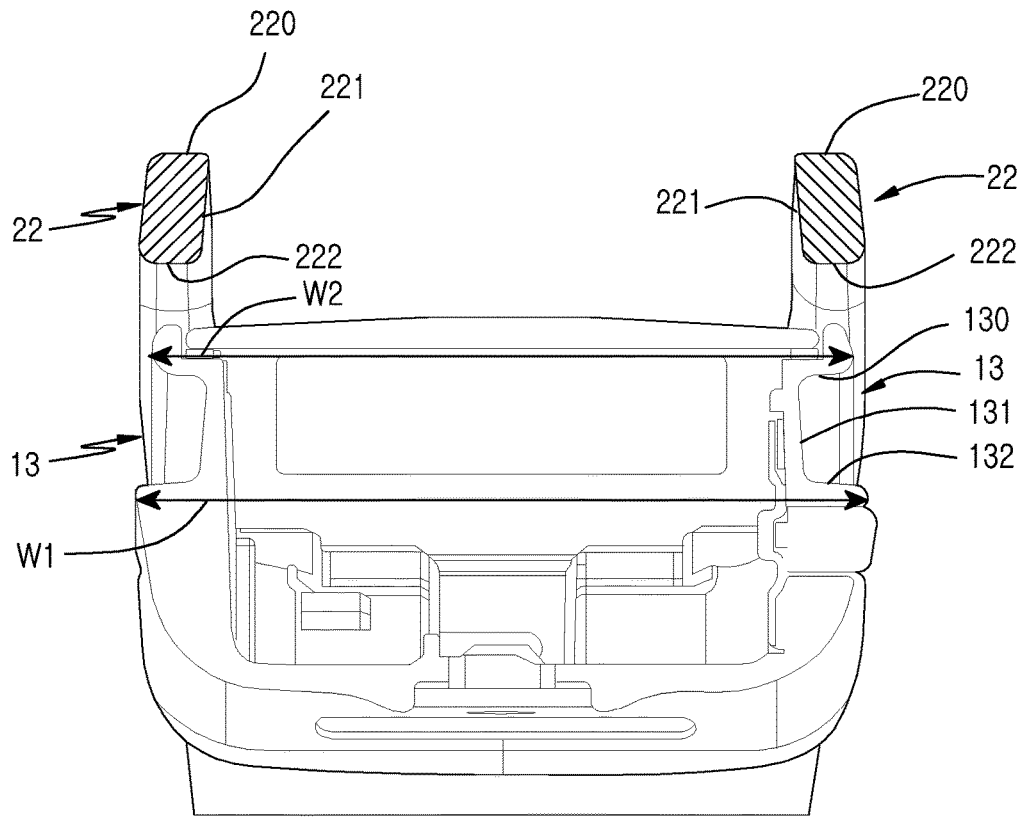
FIG. 13 is a partial cutaway perspective view showing a curved body prior to being mounted on a wearing part according to an embodiment of the present disclosure.

FIG. 13 is a partial cutaway perspective view showing the curved body prior to being mounted on the wearing part according to various embodiments of the present disclosure. Referring to FIG. 13, a body removable structure provided in the wearable device according to an embodiment of the present disclosure and a direction of removal will be explained. In the present embodiment, an undue bending operation may occur between the body 10 and the seating part 22 due to a shape characteristic of the bar type body 10 having a curvature and various characteristics of body shape of the user. In this case, a structure may be configured to provide a removal force according to a direction of the present embodiment needs to fix the longitudinal end of the body 10 more tightly. The size of the seating part is designed to be smaller than the longitudinal size of the body so that the side surface of the body can be hold relatively stronger by elasticity of the wearing part. In addition, a separate bending prevention protrusion structure may be added to a certain section of the seating part facing the body with respect to the section where an undue bending operation occurs when the wearable device is worn on the human body.

Referring to FIG. 13, the body 10, that is, the body housing 12, may be removable from the wearing part 20. The direction of removal may include a coupling direction (that is the relative direction that the body housing 12 and the wearing part 20 move to effect coupling) in which the body 10 moves from bottom to top and is coupled to the seating part 22, and a decoupling direction (that is the relative direction that the body housing 12 and the wearing part 20 move to effect decoupling) in which the body 10 is pushed down and is decoupled from the wearing part 20. The coupling direction refers to a direction in which the body coupled to the wearing part 20 is prevented or inhibited from being separated from the human body.

The curved body housing 12 may have a widthwise direction in which the width is gradually reduced from the rear surface or the center to the front surface, such that removal of the body housing 12 from the wearing part 20 may be accomplished by moving the body housing 12 and the wearing part 20 apart from each other in a first direction but not in a second direction that is opposite that of the first direction, thereby providing a first removal direction. The width W2 of the body housing 12 on the front surface in the widthwise direction (X-axis direction) is smaller than the width W1 on the center (including the rear surface) in the widthwise direction. The body housing 12 having the above-described shape should be moved from bottom to top with reference to the seating part to be coupled to the seating part. The side surface of the body housing includes a first part enclosing between the recess 13 and the front surface 120 and a second part enclosing a part between the recess 13 and the rear surface 121, and the width W2 of the first part is set to be smaller than the width W1 of the second part when viewed in a cross section of the body housing 12 cut perpendicularly to the first direction (Y-axis direction). The above-described structure provides the first removal direction.

In addition, the removal structure for coupling or decoupling the curved body housing 10 to or from the seating part 22 may be formed along the circumference of the opening provides a second direction of removal. The removal structure includes the seating recess 13 and the seating part 22. The seating recess 13 may extend along the circumference of the side surface 122 of the curved body housing and continuously extends with the same curvature as the first curvature. The seating part 22 may be tightly coupled to the seating recess 13 to fix the curved body housing 10 to the opening 21. The seating part 22 may be made of an elastic material and is elastically deformable according to whether the seating part 22 is coupled to the seating recess 13 or not, and the opening of the seating part is configured to be slightly smaller than the curved body housing so that the seating part is tightly coupled to the seating recess 13. In particular, the seating part 22 may be coupled to the seating recess formed along the outer circumference of the side surface of the side surfaces 122 of the curved body housing to have the same curvature as the first curvature.

The seating recess 13 may be provided with a first close contact surface including a first top surface 130, a first intermediate surface 131, and a first bottom surface 132. The seating recess 13 may be configured to have the horizontal width of the exterior corresponding to the first bottom surface 132 wider than the horizontal width of the exterior corresponding to the first top surface 130. The first top surface 130 may be configured to be horizontally flat or substantially horizontally flat, and the first bottom surface 132 may be configured to be horizontally flat or substantially horizontally flat.

In addition, the seating part 22 includes a second close contact surface including a second top surface 220, a second intermediate surface 221, and a second bottom surface 222 and which is in close contact with the first close contact surface. The second top surface 220 may be configured to be horizontally flat or substantially horizontally flat and the second bottom surface 222 may be configured to be horizontally flat or substantially horizontally flat. The seating part 22 is configured to have the horizontal width of the exterior corresponding to the second bottom surface 222 wider than the horizontal width of the exterior corresponding to the first top surface 220 such that removal may in accomplished by moving the body 10 relative to the seating part 22 in one direction but is inhibited in the opposite direction, thereby providing the second removal direction.

The second close contact surface of the seating part 22 is formed in a shape corresponding to the first close contact surface of the seating recess 13, so that the body can be safely coupled to the wearing part and safely decoupled from the wearing part when necessary. Such a removal structure can prevent unexpected removal caused by a wearing pressure when the user does physical activity (can prevent the body from being decoupled from the wearing part).

Figure 14:
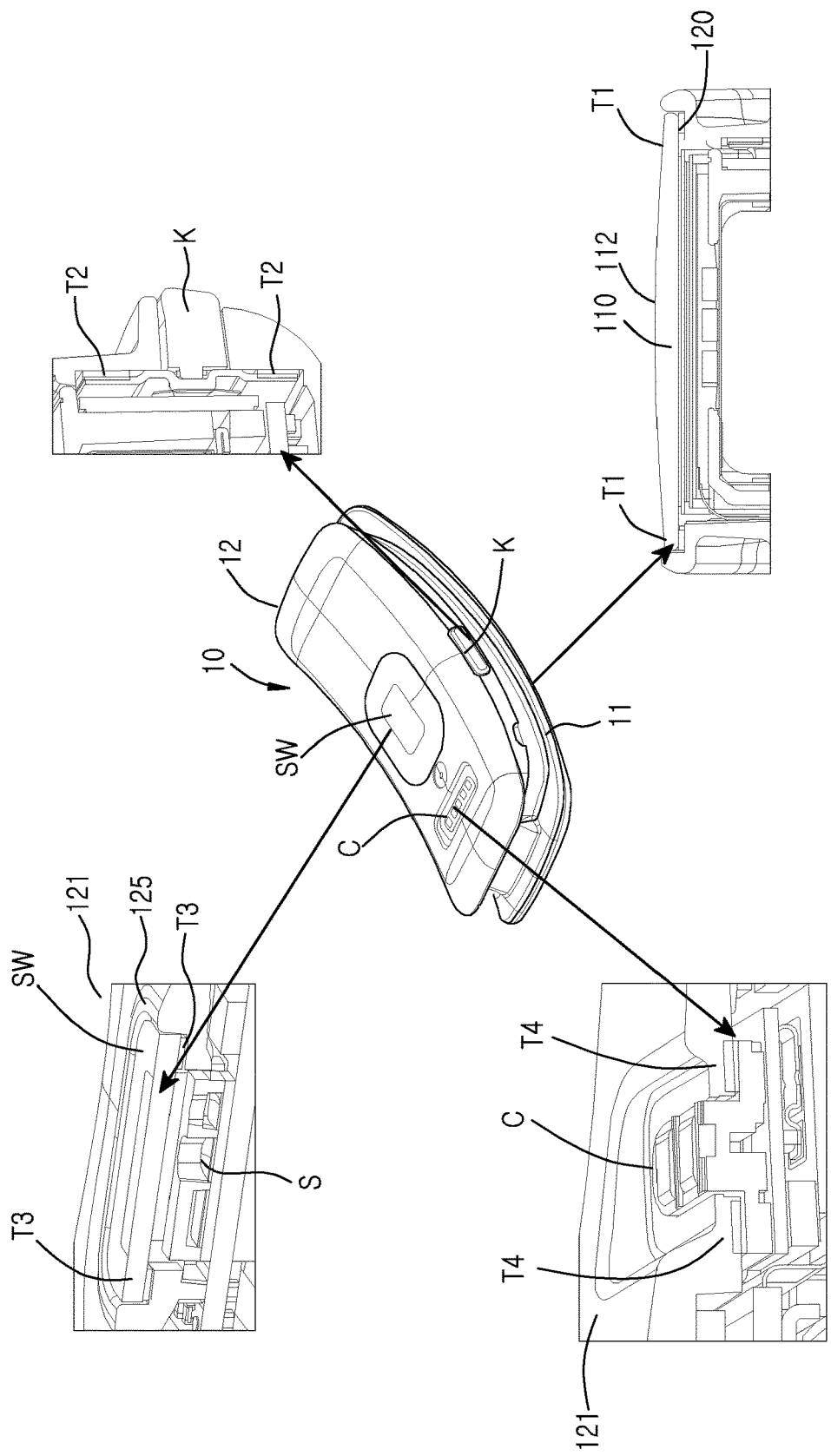
FIG. 14 is a partial cutaway perspective view showing a waterproof structure applied to a plurality of parts of a wearable device according to an embodiment of the present disclosure.
Figure 15:
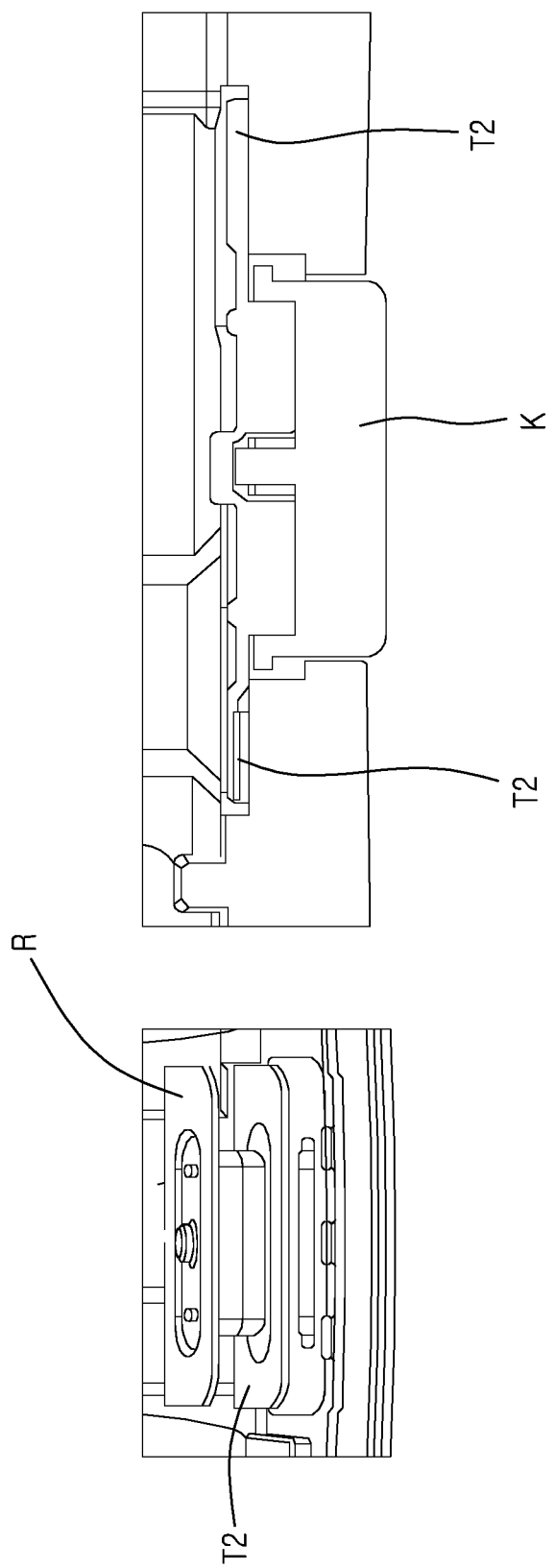
FIG. 15 is a partial cutaway perspective view showing a waterproof structure applied to a side key of a wearable device according to an embodiment of the present disclosure.
Figure 16:
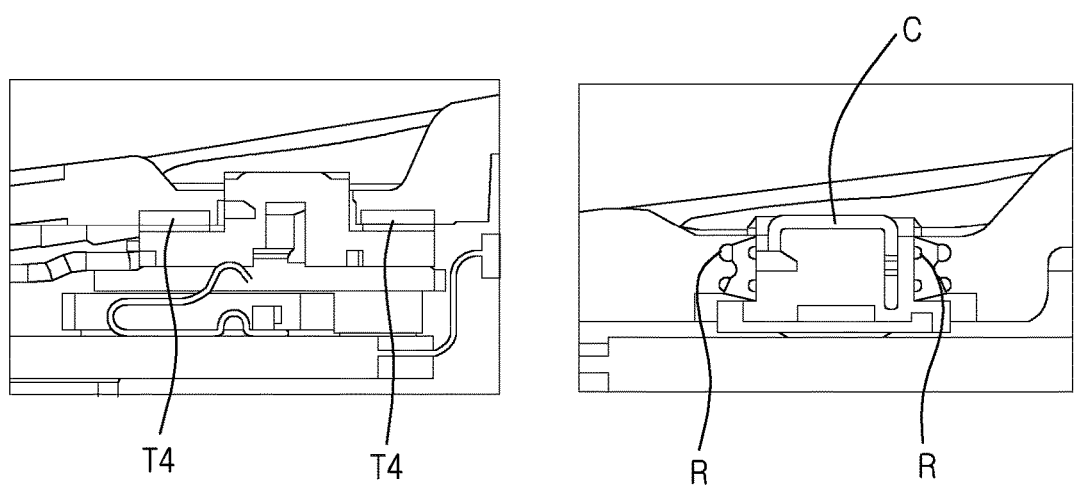
FIG. 16 is a partial cutaway perspective view showing a waterproof structure applied to a charging terminal of a wearable device according to various embodiments of the present disclosure.

Hereinafter, a waterproof structure of a wearable device according to an embodiment of the present disclosure will be explained with reference to FIGS. 14 to 16. FIG. 14 is a partial cutaway perspective view showing a waterproof structure applied to a plurality of parts of the wearable device according to various embodiments of the present disclosure. FIG. 15 is a partial cutaway perspective view showing a waterproof structure applied to a side key of the wearable device according to various embodiments of the present disclosure. FIG. 16 is a partial cutaway perspective view showing a waterproof structure applied to a charging terminal of the wearable device according to various embodiments of the present disclosure. As shown in FIGS. 14 to 16, the wearable device according to the present embodiments applies a uni body structure by coupling the body housing and the battery bracket, thereby minimizing the number of waterproof points. The wearable device according to the present embodiments includes a plurality of waterproof structures. The waterproof structure of the wearable device according to the present embodiments is applied to a place where the curved window 112 is disposed, a place where the side key (k) is disposed, a place where the sensor (s) is disposed, and a place where the charging terminal (c) is disposed.

First, the waterproof structure for the curved window 112 mounted on the front surface 120 of the body housing applies a waterproof tape (T1). The curved window 112 is attached to an adhesive surface of the circumference of the front surface 120 to which the waterproof tape T is attached by using the waterproof tape T1. The waterproof tape T1 is a double-sided tape and has an upper surface attached to the curved window 112 and a lower surface attached to the adhesive surface 120a of the front surface (shown in FIG. 12). Water is prevented from entering the body housing 12 by the waterproof tape T1.

Secondly, the waterproof structure for the side key (k) disposed on the side surface 122 of the body housing applies a waterproof tape T2. The waterproof tape T2 may be a double-sided tape and may be provided to enclose the side key (k). One surface of the waterproof tape T2 may be attached to the inner surface of the body housing where the side key is disposed, and the other surface is attached to a silicon rubber, so that water is prevented or inhibited from entering by the waterproof tape T2. In addition, the side key (k) includes a silicon rubber for providing a restoring force when it is pressed, and a waterproof protrusion P is tightly arranged along the circumference of the silicon rubber (see FIG. 15) so that water is prevented from entering between the silicon rubber and the inner surface of the body housing. The silicon rubber prevents water from entering through the lower side by using the waterproof protrusion P and prevents water from entering the upper side by using the waterproof tape T2 placed on the lower side.

Thirdly, a waterproof structure using a waterproof tape T3 is applied to the sensor (s) disposed on the rear surface 121 of the body housing. The sensor (s) is provided with a sensor interface (sensor window) and the waterproof tape T3 is a double-sided tape and has one surface attached to the inner surface of the body housing and the other surface attached to the bottom surface of the sensor interface (sw). The waterproof tape T3 is attached along the lower circumference of the sensor interface (sw).

Fourthly, a waterproof structure is applied to the charging terminal (c) disposed on the rear surface 121 of the body housing. The waterproof structure for the charging terminal (c) may be achieved by fitting a high elastic waterproof part R made of rubber or silicon material into the charging terminal (c). The waterproof part R is disposed between the side surface of the charging terminal and the inner wall of the body housing to prevent water from entering the charging terminal. In addition, a waterproof tape P4 is attached between the body of the charging terminal and the inner surface of the body housing to prevent water from entering the body of the charging terminal (c). In addition to the waterproof tape, various kinds of adhesive such as a bond, silicon, and the like may be used as a waterproof member.

Figure 17A:
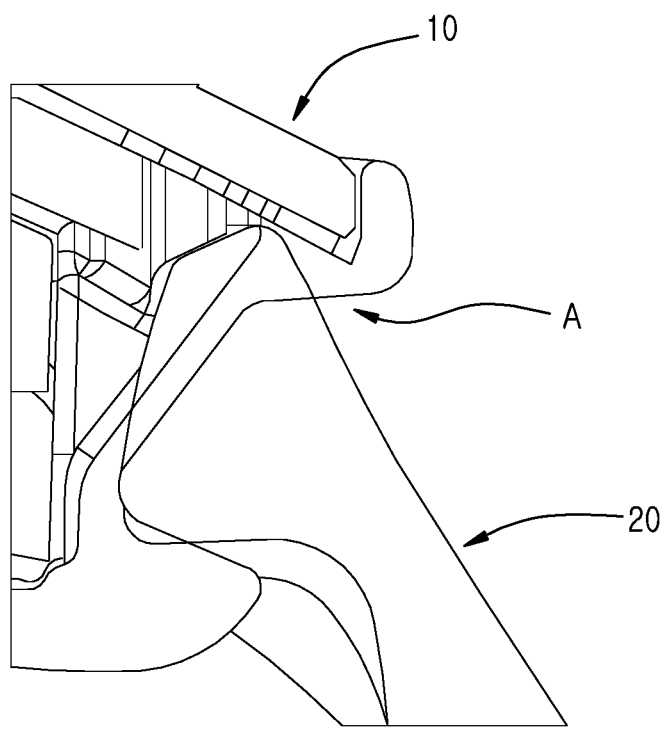
FIG. 17A and FIG. 17B illustrate a section view showing boundary areas between a body and a wearing part according to various embodiments of the present disclosure.
Figure 17B:
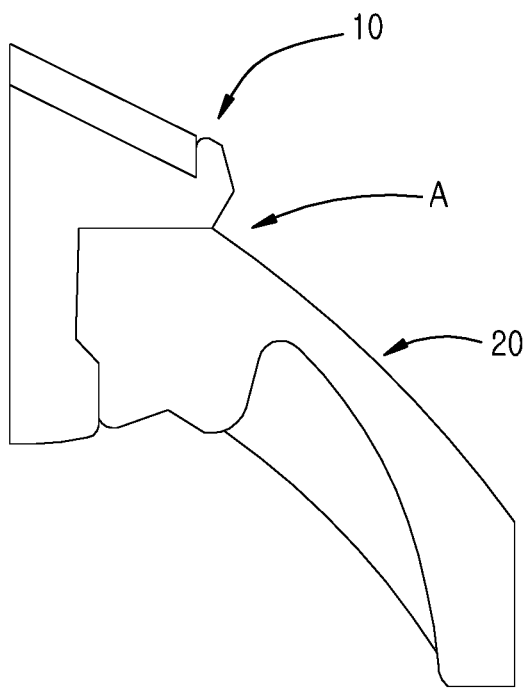

FIG. 17A and FIG. 17B is a section view showing a boundary area A between the body and the wearing part according to various embodiments of the present disclosure. Referring to FIG. 17A and FIG. 17B, the configuration of the wearing part 20 according to various embodiments of the present disclosure will be explained. The wearing part 20 includes a seating part and a band. When a user wears the wearable device on user's wrist, the wearing part 20 is subject to a pulling force in the boundary area A between the body 10 and the wearing part 20. In this state, there may be a gap between the body 10 and the wearing part 20 (the pulling force is concentrated) and the gap may deface the exterior. To prevent this problem, a coring section in the form of a cavity is provided on the inner surface of the end of the wearing part 20 in the boundary area, that is, on a certain section of a wearing surface. The end of the wearing surface is relatively thinner than the other parts by the coring section. Therefore, when the user wears the wearable device on the user's wrist, the wearing part, which is relatively thin, may be relatively more bent such that a gap is inhibited or prevented from being generated between the body 10 and the wearing part 20.

Figure 18:
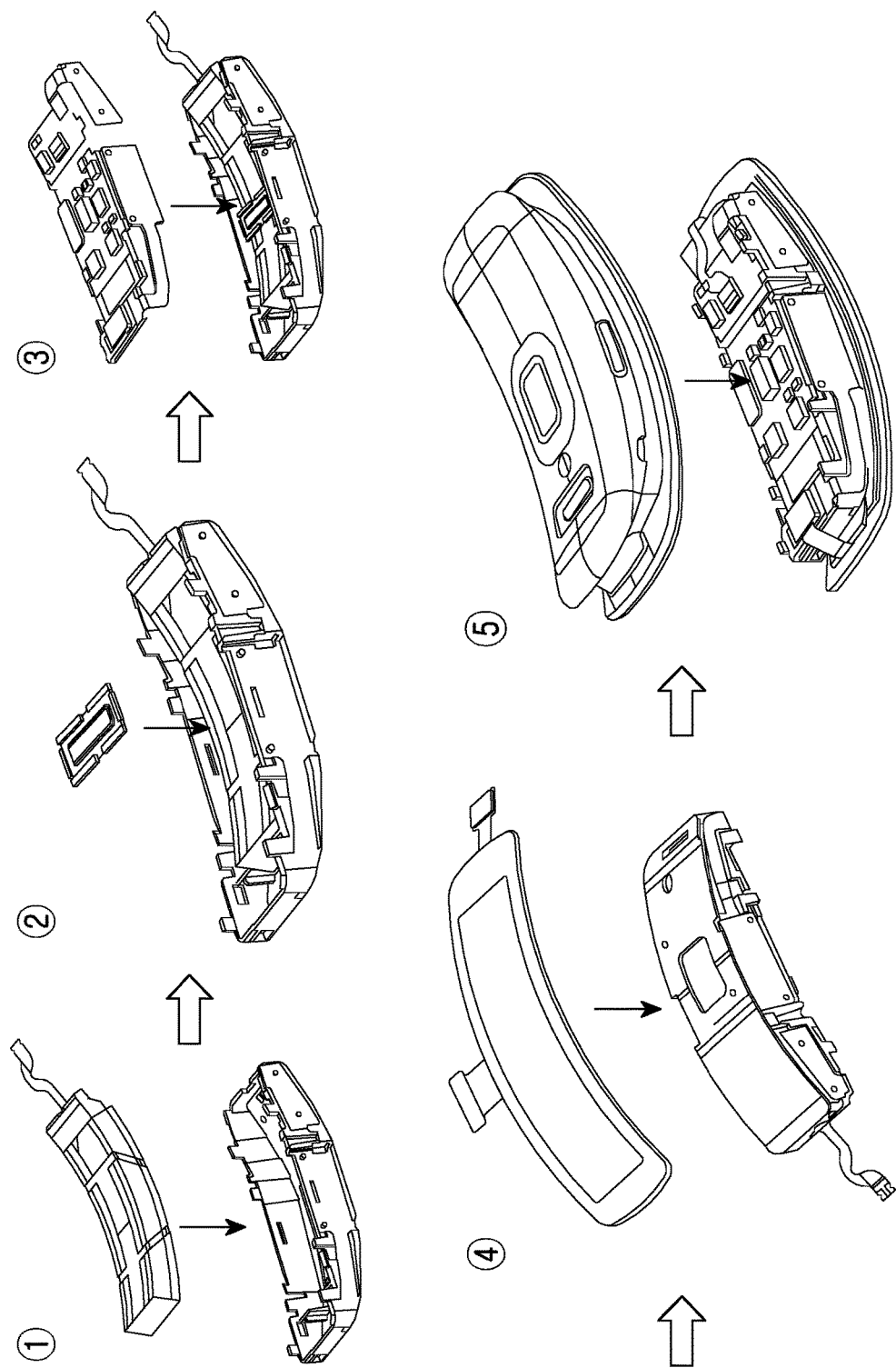
FIG. 18 illustrates a view showing an example of an assembly order of a wearable device according to various embodiments of the present disclosure.

FIG. 18 is a view showing an example of an assembly order of the wearable device according to various embodiments of the present disclosure. An assembly process of the wearable device according to the present embodiment will be explained with reference to FIG. 18. Referring to FIG. 18, a battery bracket (inner bracket) for fixing electronic parts is further provided in the present embodiment. A structure by coupling the body housing and the battery bracket to each other is to guarantee assembly of a uni-body housing structure optimized to waterproofing. In addition, various electronic parts may be fixed to the battery bracket by assembling, attaching, fusing, riveting, screwing, and the like. The present embodiment may provide an assembly structure that excludes a screw boss. The battery bracket in which the electronic parts are modularized and the body housing are fixed by a hook and a gap between the curved window and the body housing is finished by a waterproof tape, so that the inner mounting space can be maximized and the waterproof performance can be maximized by excluding a screw boss.

First, the battery is mounted in the battery bracket and a conductive or metal piece is fixed to the center of the rear surface of the battery. Next, a substrate assembly is assembled with the battery bracket and the display is fixed to the battery bracket. Finally, the body housing is assembled with the battery bracket assembly and a final assembly is completed.

Figure 19:
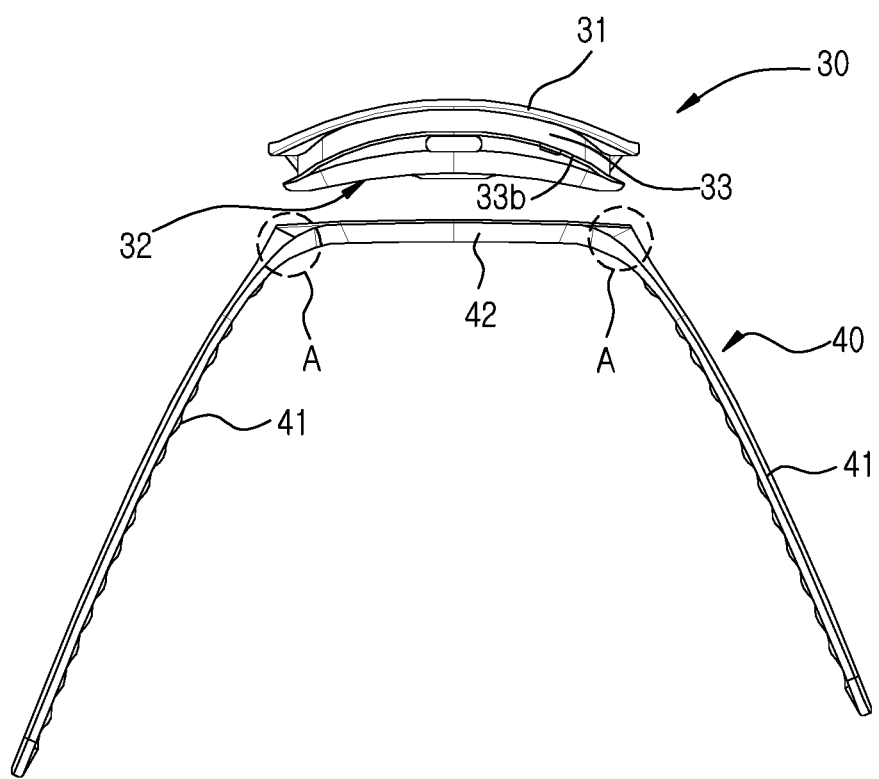
FIG. 19 is a side view showing a body and a wearing part of a wearable device, which are separated from each other, according to an embodiment of the present disclosure.
Figure 20:
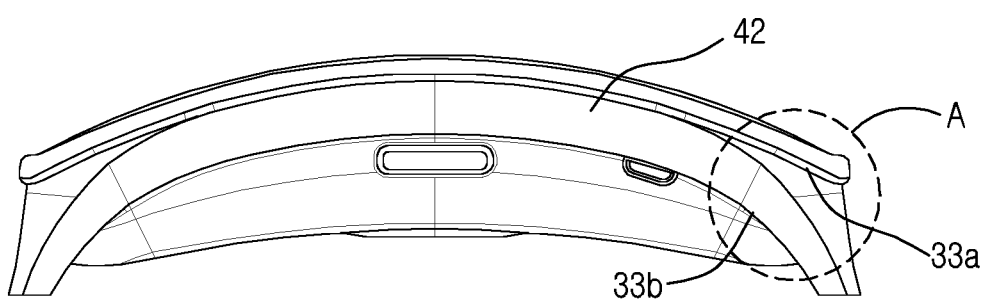
FIG. 20 illustrates a side view showing a curved body that is coupled to a wearing part according to an embodiment of the present disclosure.

FIG. 19 is a side view showing a wearable device according to various embodiments of the present disclosure, in which a body 30 and a wearing part 40 is decoupled from each other. FIG. 20 is a side view showing the body 30 and the wearing part 40 which are coupled to each other according to various embodiments of the present disclosure. In explaining the configuration of the wearable device according to the present embodiment with reference to FIGS. 19 and 20, redundant explanation of the same elements as those of FIGS. 2 and 3 will be omitted and only differences will be explained.

In general, users' wrists have different curvatures when users wear wearable devices on their wrists. Since the respective curvatures of the users' wrists are different, a wearing sensation that each user can feel may be different. In particular, since woman's wrist is thinner than man's wrist, the wearable device cannot fit all of the users. However, since the wearable device according to the present embodiments has a structure in which the wearing part 40 is removable from the body 30 and the wearing part is changeable, users can select the wearing part to fit their respective body sizes.

The wearing part 40 of the wearable device according to the present embodiment of FIGS. 19 and 20 has a different curvature from the wrist curvature provided by the wearing part of the wearable device shown in FIGS. 2 and 3. The wearable device according to the present embodiment includes the wearing part 40 and the body 30 which can be coupled to or decoupled from the wearing part 40. The end of the wearing part 40 provides a varying curvature in the boundary area A where the body 30 and the wearing part 40 are coupled to each other, so that the wearable device can respond to various wrist curvatures.

The wearing part 40 includes a seating part 42 and a band part 41 and is configured to have a different curvature from the first curvature of the body (the curvature of the front surface of the body housing and the curved display) in the boundary area A between the seating part 42 and the band part 41. In addition, the curvature of a seating recess 33 on the side surface of the body is different from the first curvature in the boundary area A. When the curvature provided by the seating recess 33 and the seating part 42 in the boundary area A is smaller than the first curvature provided by the body 30, the wearable device makes a user who has a small wrist curvature feel good when the user wears it. When the curvature provided by the seating recess 33 and the seating part 42 in the boundary area A is greater than the first curvature provided by the body 30, the wearable device makes a user who has a large wrist curvature feel good when the user wears it.

In addition, the seating recess 33 of the body 30 includes a curvature of a top surface 33a and a curvature of a bottom surface 33b, and the curvature of the bottom surface 33b is smaller than the curvature of the top surface 33a in the boundary area A, so that the wearable device can respond to a user's wrist curvature.

As a result, the curvatures provided by the seating recess 33 and the seating part 42 of the wearing part do not need to be uniform and the wearable device can respond to various users' wrist curvatures by partially varying the curvature of the seating recess 33 or the curvature of the bottom surface 33b of the seating recess in the boundary area A.

The configuration of a wearing part according to various embodiments of the present disclosure will be explained with reference to FIGS. 21 to 24.

Figure 21:
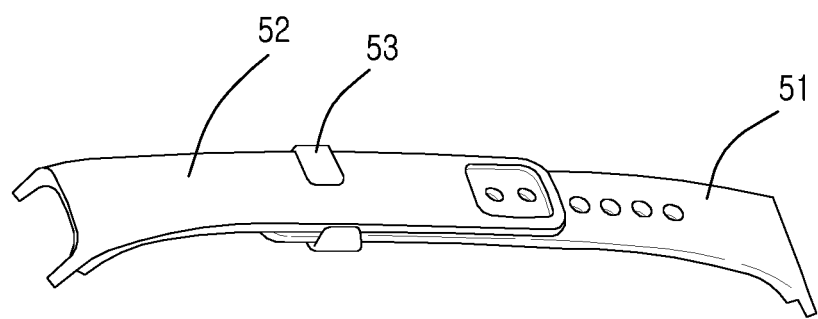
FIG. 21 is a perspective view according to an embodiment of a wearing part provided on a wearable device according to an embodiment of the present disclosure.

A wearing part shown in FIG. 21 includes first and second bands 51 and 52 and an area or a form 53 for arranging the first and second bands 51 and 52 as a single body. When a user wears the wearable device on user's wrist, the first and second bands 51 and 52 are arranged as a single body by the clip 53. The clip 53 is an accessory for clipping the first and second bands 51 and 52 and has a part opened. The first band 51 may be provided with a plurality of fastening holes in a lengthwise direction.

Figure 22:
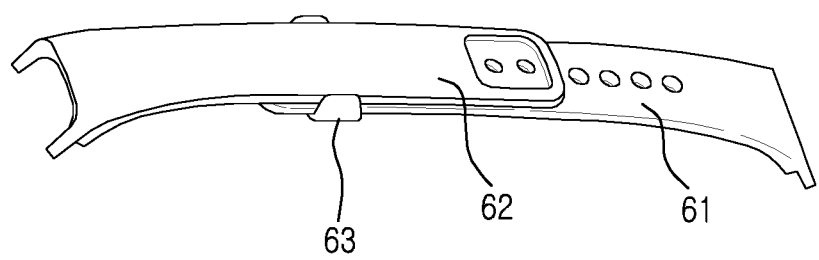
FIG. 22 is a perspective view showing an embodiment of a wearing part provided on a wearable device according to an embodiment of the present disclosure.

A wearing part shown in FIG. 22 includes first and second bands 61 and 62 and an area or a form 63 for arranging the first and second bands 61 and 62 as a single body. When a user wears the wearable device on user's wrist, the first and second bands 61 and 62 are arranged as a single body by the clip 63. The clip 63 is an accessory for clipping the first and second bands 61 and 62 and has a part opened more than the clip 53 of FIG. 20.

Figures 23A, 23B:
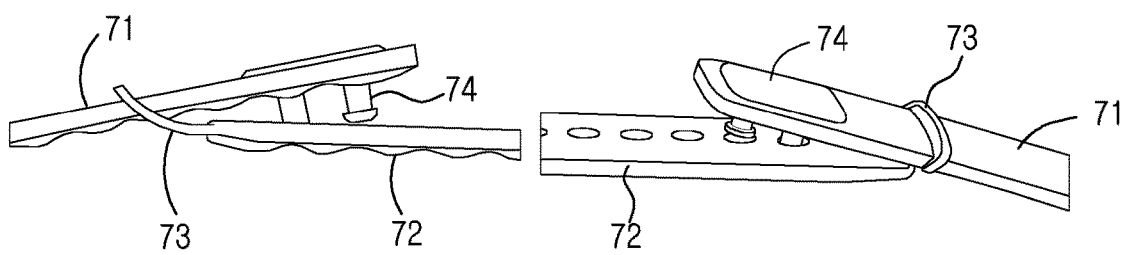
FIG. 23A is a side view showing an embodiment of a wearing part provided on a wearable device according to an embodiment of the present disclosure.
FIG. 23B is a perspective view of the wearing part of FIG. 23A.

A wearing part shown in FIG. 23A and FIG. 23B includes first and second bands 71 and 72 and an area or a form 73 for arranging the first and second bands 71 and 72 as a single body. When a user wears the wearable device on user's wrist, the first and second bands 71 and 72 are restricted by each other by the clip 73. The clip 73 may be an accessory that is integrally formed with the second band 72 and the first band 71 is arranged along with the second band 72 as a single body by the clip 73. A fastening part 74 may be integrally formed with the end of the first band and a fastening protrusion of the fastening part 74 may be inserted into the hole of the second band, so that the first and second bands 71 and 72 are restricted by each other as a single body.

Figure 24A:
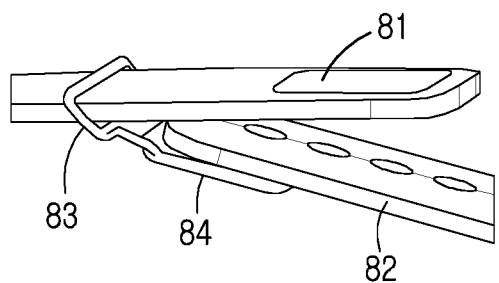
FIG. 24A is a perspective view showing an embodiment of a wearing part provided on a wearable device according to an embodiment of the present disclosure.
Figure 24B:
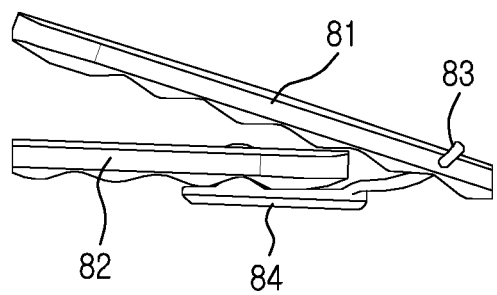
FIG. 24B is a side view of the wearing part of FIG. 24A.

A wearing part shown in FIG. 24A and FIG. 24B may include first and second bands 81 and 82 and a clip 83 for arranging the first and second bands 81 and 82 as a single body. When a user wears the wearable device on user's wrist, the first and second bands 81 and 82 are restricted by each other by the clip 83. The clip 83 is an accessory integrally formed with the second band 82 and the first band 81 is arranged along with the second band 82 as a single body by the clip 83. A fastening part 84 is integrally formed with the end of the first band and a fastening protrusion of the fastening part 84 is inserted into the hole of the second band, so that the first and second bands 81 and 82 are restricted by each other as a single body.

The wearing part shown in FIGS. 21 to 26 may be configured in various colors and a wearing surface may be formed in an uneven shape (having a wave form when viewed in a cross section), thereby improving a sensation that the user may feel when wearing the wearable device.

Figure 25:
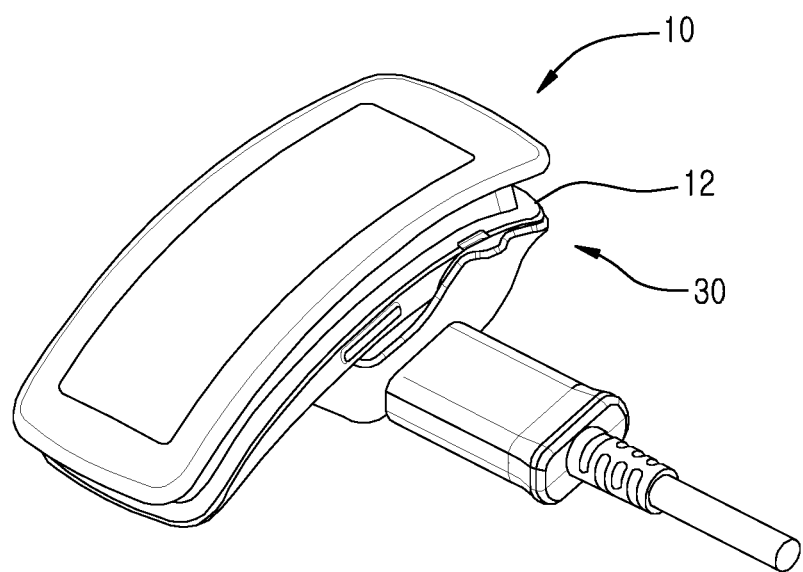
FIG. 25 is a perspective view showing a wearable device that is coupled to a cradle according to various an embodiment of the present disclosure.
Figure 26:
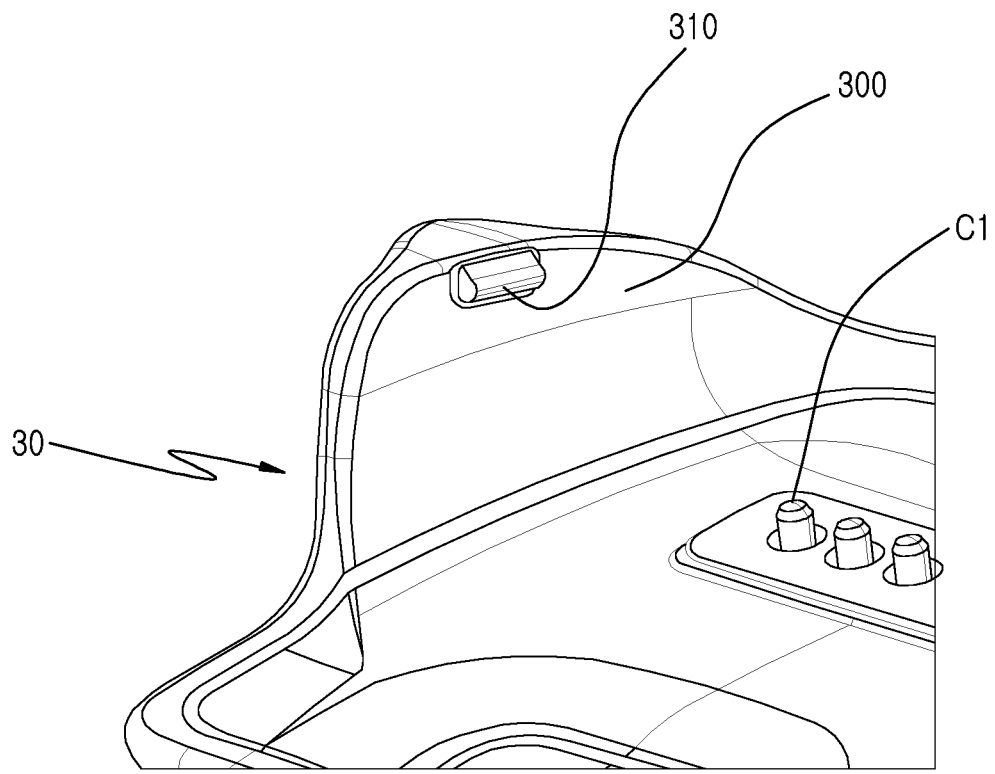
FIG. 26 is a perspective view showing a part of a cradle according to an embodiment of the present disclosure.
Figure 27:
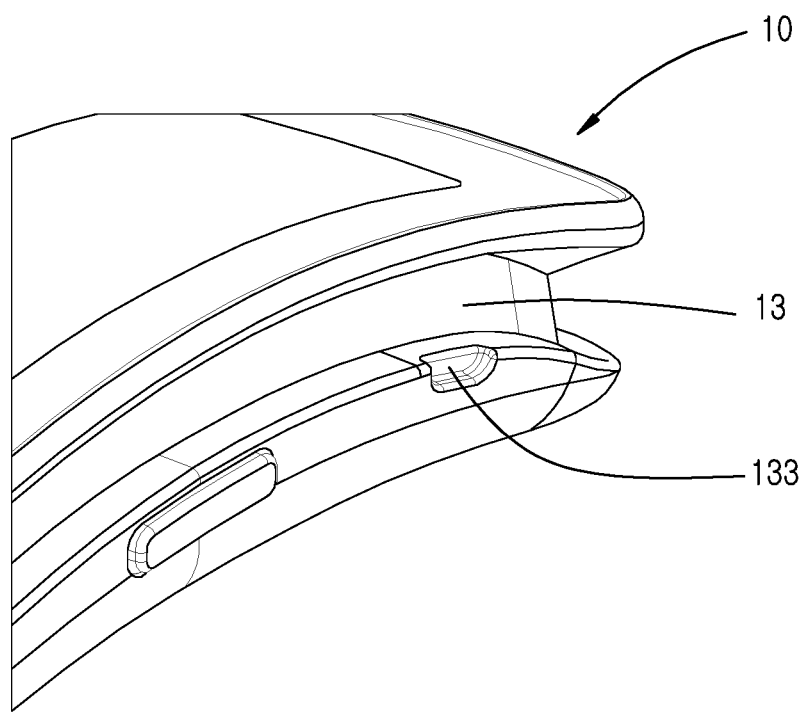
FIG. 27 is a perspective view showing a part of a body housing of a wearable device according to an embodiment of the present disclosure.

FIG. 25 is a perspective view showing a wearable device which is coupled to a charging cradle according to various embodiments of the present disclosure. FIG. 26 is a perspective view showing a part of the charging cradle according to various embodiments of the present disclosure. FIG. 27 is a perspective view showing a part of the body housing of the wearable device according to various embodiments. Referring to FIGS. 25 to 27, the wearable device 10 according to the present embodiment includes a holding structure to be held in the charging cradle 30 and maintain a connecting state stably. The holding structure may include a holding protrusion 310 formed inside an arm 300 of the charging cradle and a holding recess 133 formed on the body housing 12. Although a single protrusion 310 and a single recess 133 are illustrated in the drawings, a pair of protrusions 310 and a pair of recesses 133 may be provided. By coupling the recess 133 and the protrusion 310, the body 12 may be held in the charging cradle 30 and maintain a stable connecting status. Reference sign c1 indicates a charging terminal provided on the bottom of the charging cradle 30. A method for placing the wearable device 10 on the charging cradle 30 may include moving the wearable device 10 from top to bottom and coupling it to the charging cradle 30.

According to various embodiments, at least part of the wearable device of the present disclosure may be implemented by using instructions stored in a computer-readable storage medium in the form of a programming module. When the instructions are executed by one or more processors, the one or more processors may perform a function corresponding to the instructions. The computer-readable storage medium may be a memory, for example. At least part of the programming module may be implemented (e.g., executed) by using the processor. At least part of the programming module may include a module, a program, a routine, sets of instructions, a process, and the like for performing one or more functions.

Examples of the computer-readable recording medium include magnetic media such as hard disks, floppy disks and magnetic tapes, optical media such as Compact Disc Read Only Memories (CD-ROMs) and Digital Versatile Discs (DVDs), magneto-optical media such as floptical disks, and hardware devices such as (Read Only Memories (ROMs), Random Access Memories (RAMs) and flash memories that are especially configured to store and execute program commands (e.g., the programming module). Examples of the program commands include machine language codes created by a compiler, and high-level language codes that can be executed by a computer by using an interpreter. The above-described hardware devices may be configured to operate as one or more software modules for performing operations of the present disclosure, and vice versa.

A module or programming module of the present disclosure may include one or more of the above-described elements, may omit some elements, or may further include additional elements. The operations performed by the module, the programming module, or the other elements according to the present disclosure may be performed serially, in parallel, repeatedly, or heuristically. In addition, some operation may be performed in different order or may omitted, and an additional operation may be added.

While the disclosure has been shown and described with reference to certain embodiments thereof, it will be understood by those skilled in the art that various changes in form and details may be made therein without departing from the spirit and scope of the disclosure. Therefore, all differences including obvious variants thereof are to be construed as being within the scope and spirit of the present disclosure and will be construed as being included in the present disclosure.

What is claimed is:
1. A wearable device comprising:
a strap having a first end and a second end, the strap comprising an opening and a buckle part formed at one of the first and second ends, the buckle part configured to fasten the first and second ends of the strap to each other; and
an elongated body configured to be removably coupled to the opening by being fitted into the opening, wherein the elongated body, having a front side and a rear side along one dimension, and one end and another end along another dimension, further comprises:
a display visible through its front side, the display configured to have substantially polygonal shape,
a vibration motor disposed at the one end of the elongated body; and
a biometric sensor configured to sense through the rear side of the elongated body,
wherein the opening is surrounded by flexible material forming a portion of the strap and the elongated body is fitted to the opening by making direct contact with the flexible material, and
wherein the lateral sides of the flexible material are substantially parallel with each other.

2. The wearable device of claim 1, wherein the substantially polygonal shape of the display is substantially rectangular.

3. The wearable device of claim 1, wherein the strap comprises a seating part from which the elongated body is removable, the seating part being formed along a circumference of the opening, wherein the seating part comprises at least one linear portion, and wherein the elongated body comprises a seating recess with which the seating part of the strap is configured to be mated.

4. The wearable device of claim 3, wherein the opening is opened in a vertical direction and has a substantially rectangular shape having a thickness, and the elongated body is removed from the opening by elastically deforming of the seating part of the strap.

5. The wearable device of claim 3, wherein the elongated body comprises a curved body housing, and wherein a front surface and a rear surface of the curved body housing have a first curvature and a second curvature, respectively, the first curvature being smaller than the second curvature.

6. The wearable device of claim 5,
wherein the display is curved and has a same curvature as the first curvature, and is mounted on the front surface of the curved body housing, and
wherein the rear surface of the curved body housing comprises a planar surface on a center area of the body and the biometric sensor is disposed on the planar surface.

7. The wearable device of claim 5, wherein the curved body housing has a horizontal direction width gradually reduced from a center toward the front surface, such that the body is decoupled by moving the body out from the opening by moving the body in a first removal direction and remains coupled when the body is moved in a direction opposite the first removal direction.

8. The wearable device of claim 5, further comprising a removal structure for selectively coupling and decoupling the curved body housing with respect to the opening by moving the curved body with respect to the opening along a second removal direction.

9. The wearable device of claim 8, wherein the removal structure comprises:
the seating recess extending along the circumference of a side surface of the curved body housing and having a curvature corresponding to a curvature of the opening; and
the seating part coupled to the seating recess to fix the curved body housing to the opening.

10. The wearable device of claim 9, wherein the curvature of corresponds to a curvature of an outer side surface of the curved body housing.

11. The wearable device of claim 9, wherein the seating recess comprises a first close contact surface which comprises a first top surface, a first intermediate surface, and a first bottom surface, and has a horizontal width of an exterior corresponding to the first bottom surface that is wider than a horizontal width of an exterior corresponding to the first top surface, and
wherein the seating part comprises a second close contact surface which is in close contact with the first close contact surface and comprises a second top surface, a second intermediate surface, and a second bottom surface, and has a horizontal width of an exterior corresponding to the second bottom surface that is wider than a horizontal width of an exterior corresponding to the second top surface, thereby providing the second removal direction.

12. The wearable device of claim 11, wherein at least one of the first and second bottom surfaces are one of horizontally planar surfaces and gently inclined surfaces.

13. The wearable device of claim 5, wherein at least one of the ends of the strap is configured to have a curvature that is different than the first curvature in a boundary area where the curved body housing and the strap are coupled to each other so that the wearable device responds to a wrist curvature of a human body.

14. The wearable device of claim 1, wherein the opening is substantially polygonal shape in top view.

15. The wearable device of claim 1, wherein the elongated body comprises a peripheral wall comprising a portion making contact with the opening of the strap, wherein the portion making contact with the strap is smooth.

16. The wearable device of claim 1, wherein the body is elongated along the length of the strap.

17. The wearable device of claim 1, wherein the strap is thicker around the opening than at the first end and the second end.

18. The wearable device of claim 1, wherein the lateral sides of the opening are substantially parallel with each other.

19. The wearable device of claim 1, wherein the front side of the elongated body is substantially flat.

20. The wearable device of claim 1, wherein the rear side of the elongated body is substantially curve and adapted to contact the skin of a user.

21. The wearable device of claim 1, wherein the lateral sides of the elongated body are substantially parallel with each other.

22. A wearable device comprising:
a strap having a first end and a second end, the strap comprising an opening and a buckle part formed at one of the first and second ends, the buckle part configured to fasten the first and second ends of the strap to each other; and
an elongated body configured to be removably coupled to the opening by being fitted into the opening,
wherein the elongated body, having a front side and a rear side along one dimension, and one end and another end along another dimension, further comprises:
a display visible through its front side, the display configured to have substantially polygonal shape,
a vibration motor disposed at the one end of the elongated body; and
a biometric sensor configured to sense through the rear side of the elongated body, wherein the opening is surrounded by flexible material forming a portion of the strap and the elongated body is fitted to the opening by making direct contact with the flexible material, and wherein the lateral sides of the flexible material are substantially parallel with each other.

* * * * *